United States Patent [19]
Yoneyama

[11] Patent Number: 6,050,153
[45] Date of Patent: Apr. 18, 2000

[54] HYDRAULICALLY-OPERATED MICROMANIPULATOR APPARATUS

[75] Inventor: Shinji Yoneyama, Tokyo, Japan

[73] Assignee: Narishige Co., Ltd., Tokyo, Japan

[21] Appl. No.: 09/146,551

[22] Filed: Sep. 3, 1998

[30] Foreign Application Priority Data

| Sep. 3, 1997 | [JP] | Japan | 9-238158 |
| Dec. 11, 1997 | [JP] | Japan | 9-341161 |
| Jun. 10, 1998 | [JP] | Japan | 10-162235 |
| Jun. 10, 1998 | [JP] | Japan | 10-162236 |

[51] Int. Cl.[7] .......... G05G 11/00; B60T 13/20; F01B 7/02; B25J 1/00
[52] U.S. Cl. .......... 74/490.13; 60/533; 92/75; 414/1
[58] Field of Search .......... 74/490.12, 490.13; 60/533, 567, 568, 571, 572; 92/75; 414/1, 2, 3, 4, 5, 6, 7, 8

[56] References Cited

U.S. PATENT DOCUMENTS

| 4,679,976 | 7/1987 | Narishige et al. | 414/4 |
| 4,946,329 | 8/1990 | Krueger | 414/4 |
| 5,431,015 | 7/1995 | Hein et al. | 60/571 X |
| 5,890,863 | 4/1999 | Yoneyama | 414/4 |

OTHER PUBLICATIONS

Patent Abstracts of Japan, vol. 018, No. 454 (P–1791), Aug. 24, 1994 & JP 06 148529 A (Olympus Optical Co Ltd), May 27, 1994).

Primary Examiner—David A. Bucci
Assistant Examiner—Colby Hansen
Attorney, Agent, or Firm—Pillsbury Madison & Sutro LLP

[57] ABSTRACT

A hydraulically-operated micromanipulator apparatus is disclosed. The micromanipulator apparatus comprises:

a micromanipulator fine control unit including an operating-side piston finely movable with respect to an operating-side hydraulic cylinder and fine control means, either the operating-side piston or the operating-side hydraulic cylinder being stationarily retained, while the rest being finely operable by the fine control means;

a hydraulically-operated micromanipulator including an actuating-side piston finely movable with respect to an actuating-side hydraulic cylinder and a fine displacement member, the actuating-side hydraulic cylinder being connected to said operating-side hydraulic cylinder through a hose, either the actuating-side piston or the actuating-side hydraulic cylinder being stationarily retained, while the rest being attached to the fine displacement member; and compensating means for compensating a pressure change of the hydraulic fluid between said operating-side hydraulic cylinder and said actuating-side hydraulic cylinder when ambient temperature changes.

7 Claims, 22 Drawing Sheets

HYDRAULICALLY-OPERATED MICROMANIPULATOR APPARATUS

BACKGROUND OF THE INVENTION

1. Field of the Invention

The present invention relates to hydraulically-operated micromanipulator apparatus including microtools, such as a glass electrode positioned in the field of a microscope with the use of hydraulically-operated remote controlling means.

2. Prior Art

In basic medical science or biotechnology, micromanipulators are used for treating cells, such as creature's organs, cellular textures, egg cells and the like. These cells are treated in various operations for example suctioning, injecting and dividing by finely controlling a microtool in the field of a microscope.

However, when an operator finely controls the micromanipulator by his direct contact with its control handle, his hand trembling may be multiplied and transmitted to the microtool through the body frame. For this reason, care should be taken for finely controlling the micromanipulator. Since the micromanipulator needs to be gently operated without hand trembling, delicate operations, the greatest possible care and a lot of skills are required. In view of these difficulties, a various hydraulically-operated micromanipulators have been proposed for finely controlling the microtool by remote controlling means. These micromanipulators are controlled by hydraulic fluid, such as hydraulic oil.

Referring now to FIG. 1, a conventional cell treatment device comprising a stage 303 for mounting a Petri dish 302 containing therein egg cells 301 dipped in a reagent, a fixed retaining unit 304 for stationary retaining the cells 301, a micromanipulator 305 for carrying out a practical cell treatment, and an optical system 306 for observing images of the cells 301 irradiated with light. The cell treatment device is operated on a vibration-proof mat 307.

The micromanipulator 305 is attached with various kinds of microtools 308, such as a glass electrode for the corresponding cell treatments and includes a three dimensional displacement mechanism for moving the tip end of the microtool 308 in three dimensions. The three dimensional displacement mechanism is finely operated by hydraulic pressure through a joystick 309.

The joystick 309 comprises a control handle 311 downwardly extending from the distal end of a visor-shaped supporting frame 310 and a transmitting unit 313 for transmitting the two directional movement 312 of the control handle 311 shown by the arrows through hydraulic pressure. The control handle 311 is provided with a converting unit 314 for converting the two directional movement of the control handle 311 into a mechanical displacement in a horizontal plane. The converting unit 314 connects the supporting frame 310 and the control handle 311. For the vertical movement of the cells to be treated, another mechanism may be provided at an adjacent position of the joystick 309.

In other conventional device, the control handle extends upwardly from the converting unit 314. However, since the operator can operate the device at a lower position without raising his arm, the former type, i.e., the micromanipulator with downwardly extending control handle has been widely used.

However, in micromanipulators operable by hydraulic pressure, such as oil pressure or water pressure, when ambient temperature changes, the volume of hydraulic fluid may also change. This leads to drift of the tip end of the microtool, and hence accurate observation or operation is not achieved.

Other electrically-operable micromanipulator is also known. However, in such micromanipulator, the tip end of the microtool drifts when it is subject to electric hindrance. The problems relating to drift, therefore, remain unsolved.

Such problems are serious when a long period of observation or operation is carried out while the tip end of the microtool is abutting to a sample. When drift occurs, the tip end of the microtool moves off from the sample, and hence the observation or operation is interrupted.

With the foregoing drawbacks in view, the present invention seeks to provide micromanipulator apparatus, which are hydraulically-operable by remote controlling means and include means for compensating drift of the microtool due to a temperature change.

SUMMARY OF THE INVENTION

According to the present invention, there is provided a hydraulically-operated micromanipulator apparatus, which comprises:

a micromanipulator fine control unit including an operating-side piston finely movable with respect to an operating-side hydraulic cylinder and fine control means, either the operating-side piston or the operating-side hydraulic cylinder being stationarily retained, while the rest being finely operable by the fine control means;

a hydraulically-operated micromanipulator including an actuating-side piston finely movable with respect to an actuating-side hydraulic cylinder and a fine displacement member, the actuating-side hydraulic cylinder being connected to said operating-side hydraulic cylinder through a hose, either the actuating-side piston or the actuating-side hydraulic cylinder being stationarily retained, while the rest being attached to the fine displacement member; and compensating means for compensating a pressure change of the hydraulic fluid between said operating-side hydraulic cylinder and said actuating-side hydraulic cylinder when ambient temperature changes.

Another object of the present invention is to provide a hydraulically-operated micromanipulator apparatus, which comprises an operating unit and an actuating unit, said operating unit including:
an operating-side hydraulic fluid chamber to be filled with hydraulic fluid; and fine control means for controlling the volume of the operating-side hydraulic fluid chamber, said actuating unit including:
an actuating-side hydraulic fluid chamber connected to the operating-side hydraulic fluid chamber through a hose and filled with hydraulic fluid; and slider means having a stationary member and a sidable member, the slidable member being sidable with respect to the stationary member by a volume change of the actuating-side hydraulic fluid chamber;

a compensating fluid chamber provided at the slidable member of the slider means and filled with drift-prevention fluid; and drift-prevention slider means having a stationary member and a sidable member, the sidable member being slidable with respect to the stationary member by a volume change of the compensating fluid chamber, the sidable member being mounted with microtool fixing means, and the volume of the hydraulic fluid being the same as that of the drift-prevention fluid, and said microtool fixing means being stationarily retained with the hydraulic fluid and the drift-prevention fluid equally changing the volumes when ambient temperature changes.

Further object of the present invention is to provide a hydraulically-operated micromanipulator apparatus, which comprises an operating unit and an actuating unit, said operating unit including:
an operating-side first hydraulic fluid chamber and an operating-side second hydraulic fluid chamber, respectively filled with hydraulic fluid; and
fine control means for respectively controlling the volumes of the operating-side first and second hydraulic fluid chambers, said actuating unit including:
an actuating-side first hydraulic fluid chamber connected to the operating-side first hydraulic fluid chamber through a hose and filled with hydraulic fluid;
an actuating-side second hydraulic fluid chamber connected to the operating-side second hydraulic fluid chamber through a hose and filled with hydraulic fluid;
first slider means having a first stationary member and a first slidable member,
the first sidable member being sidable with respect to the first stationary member by a volume change of the actuating-side first hydraulic fluid chamber; and
second slider means having a second stationary member and a second slidable member, the second slidable member being relatively and oppositely slidable to the first sidable member by a volume change of the actuating-side second hydraulic fluid chamber, the second slidable member being mounted with microtool fixing means, and
the volume of the hydraulic fluid between said operating-side first hydraulic fluid chamber and said actuating-side first hydraulic fluid chamber being the same as that of the hydraulic fluid between said operating-side second hydraulic fluid chamber and said actuating-side second hydraulic fluid chamber, and said microtool fixing means being stationarily retained with the hydraulic fluid within said operating-side first hydraulic fluid chamber and said actuating-side first hydraulic fluid chamber and the hydraulic fluid within said operating-side second hydraulic fluid chamber and said actuating-side second hydraulic fluid chamber equally changing the volumes when ambient temperature changes.

Other objects and features of the present invention will become apparent by reference to the following detailed description taken in conjunction with the accompanying drawings.

PREFERRED EMBODIMENTS OF THE INVENTION

The present invention will be described with reference to three preferred embodiments. Although the term "hydraulically-operated micromanipulator apparatus" is herein used as an apparatus operable by oil pressure, it also includes an apparatus operable by water pressure or other fluid pressure.

Figure 1:
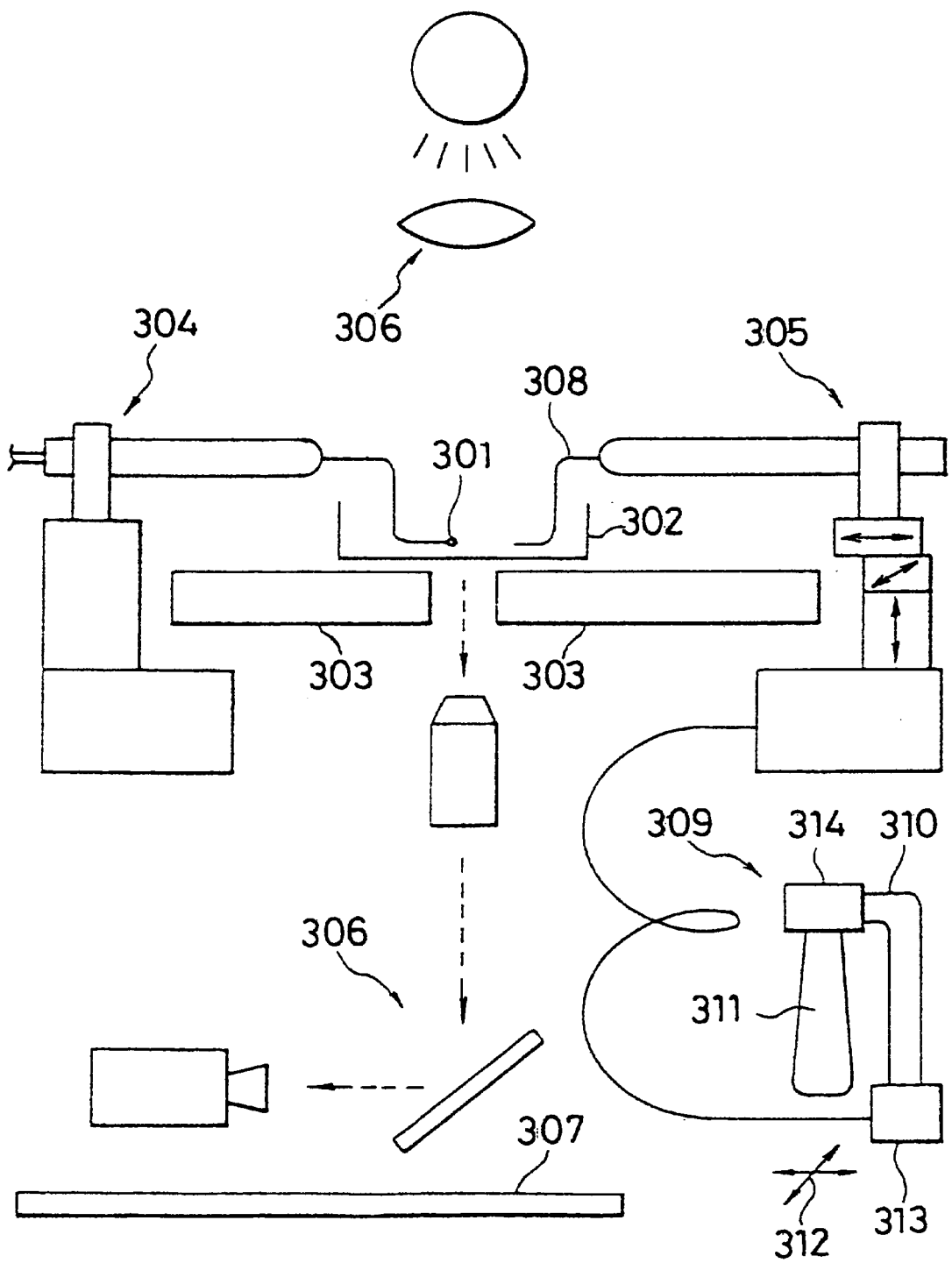
FIG. 1 is an explanatory view schematically showing a conventional cell treatment device.
Figure 2:
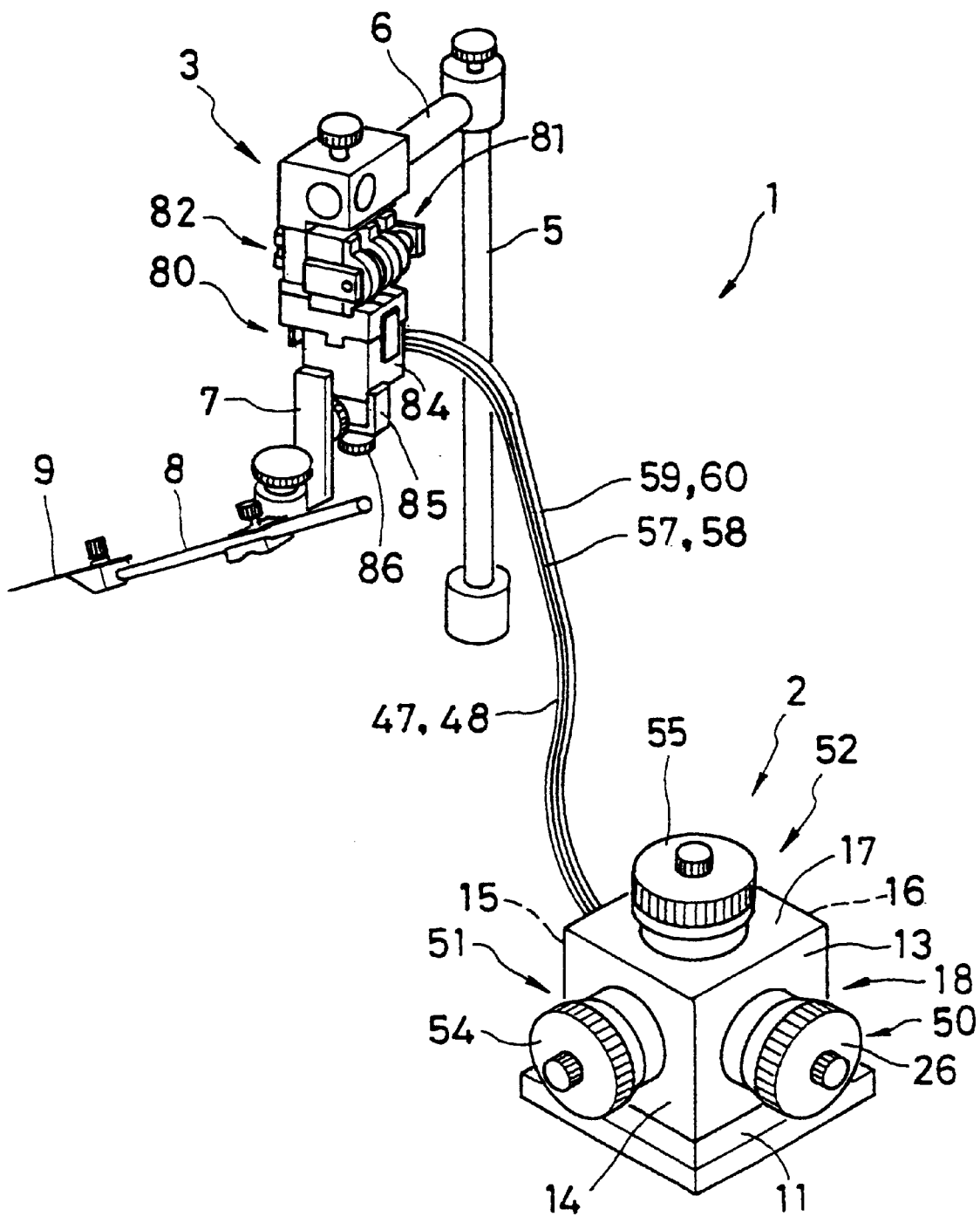
FIG. 2 is a perspective view showing a first embodiment of a hydraulically-operated micromanipulator apparatus according to the present invention.

Referring now to FIG. 2, a first embodiment of a hydraulically-operated micromanipulator apparatus according to the present invention is shown, in which the micromanipulator apparatus 1 comprises a micromanipulator fine control unit 2 having handles for three-directional control and a hydraulically-operated micromanipulator 3. The micromanipulator fine control unit 2 is connected to the hydraulically-operated micromanipulator 3 (hereinafter referred to as a micromanipulator) through a plurality of hoses 47, 48, 57, 58, 59, 60. The micromanipulator 3 is fixed to a mounting bar 6 which is supported to a pole 5. A tightening device 7 is mounted on the micromanipulator 3 for supporting a holder 8. A microtool 9 is attached to the front end of the holder 8.

A micromanipulator fine control unit 2 has a base plate 11 to which is mounted four side plates 13, 14, 15, 16 and a top plate 17. The base plate 11, the four side plates 13, 14, 15, 16 and the top plate 17 are fixed to each other, thereby providing a case 18.

Figure 3:
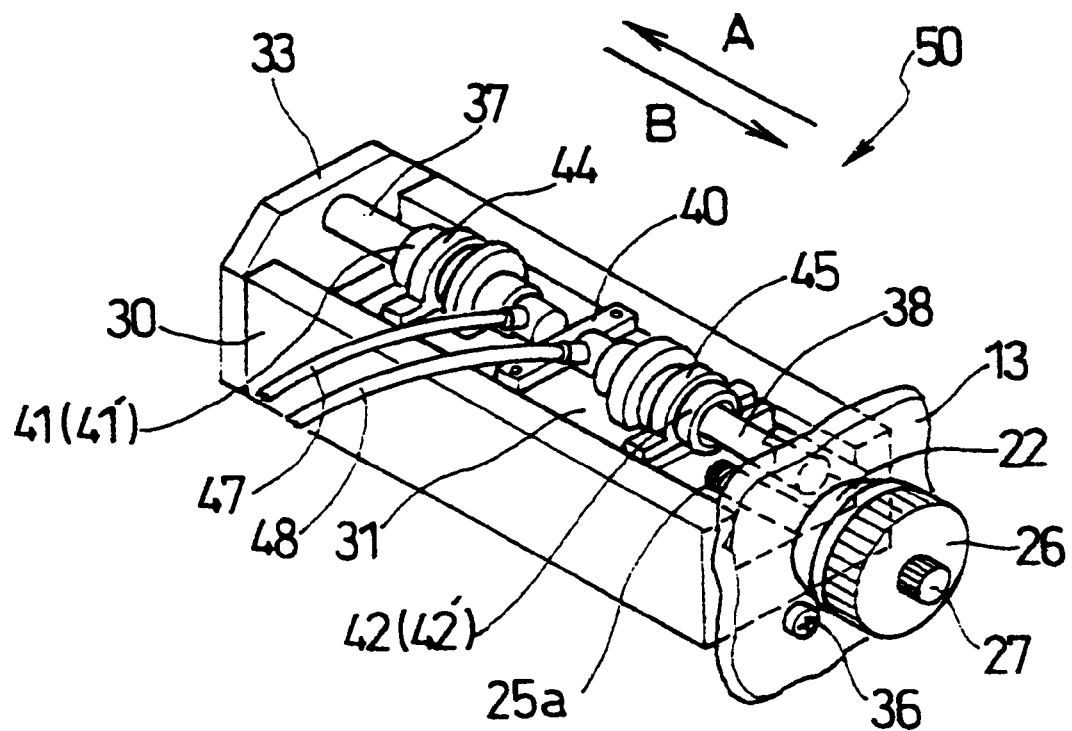
FIG. 3 is a perspective view showing an X-axis fine control mechanism of a micromanipulator fine control unit according to the first embodiment of the invention.
Figure 4:
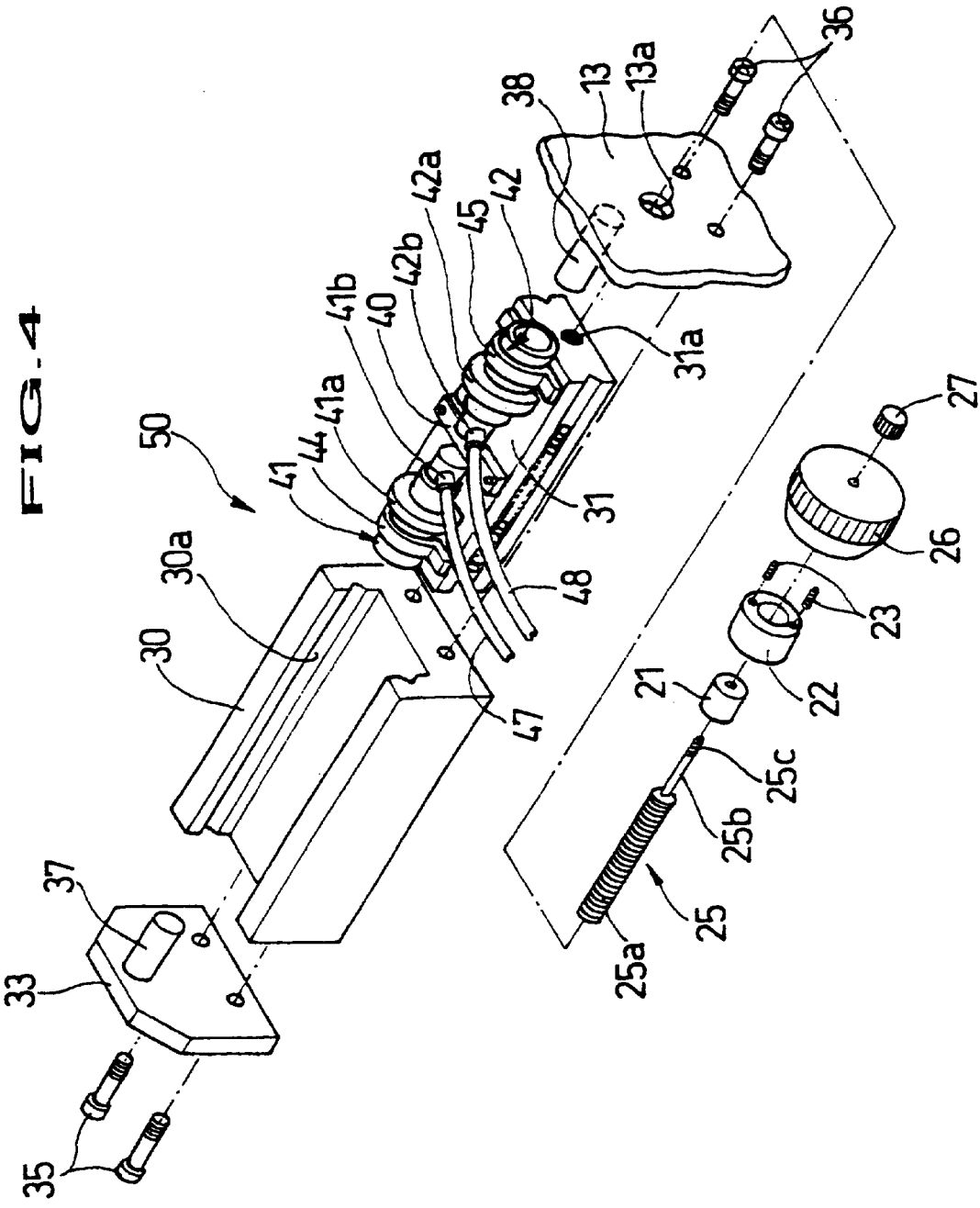
FIG. 4 is an exploded perspective view showing the X-axis fine control mechanism of FIG. 3.

The micromanipulator fine control unit 2 includes an X-axis fine control mechanism 50 for finely displacing the microtool 9 to the X-axis directions, i.e. right-and-left directions. As shown in FIGS. 3 and 4, the side plate 13 is centrally provided with a through opening 13a through which the front portion of a bearing metal 21 is fitted. The bearing metal 21 is fitted within a ring 22, which is fixed to the side plate 13 by a plurality of bolts 23. The bearing metal 21 has a central through-opening for receiving an X-axis fine control screw shaft 25. The X-axis fine control screw shaft 25 comprises a fine control male thread 25a, a stem portion 25b having reduced diameter and received in the central through-opening of the bearing metal 21, and a fixing male thread 25c provided at one end of the stem portion 25b remote from the fine control male thread 25a.

An X-axis fine control handle 26 is rotatably fitted over the ring 22. The X-axis fine control handle 26 has a cylindrical shape, one end of which is open for receiving therein the ring 22. The closed end of the X-axis fine control handle 26 forms a knurled head. The fixing male thread 25c threadly engages with a central threaded through-opening of the control handle 26 and further with a fixing nut 27. The X-axis fine control handle 26 is thus fixed to the X-axis fine control screw shaft 25.

An outer slider 30 as a basement has a pair of guiding grooves 30a for receiving an inner slider 31 as a sliding table through a non-shown linear-way bearing. The inner slider 31 is provided at the tailing end with a threaded opening 31a for the engagement with the fine control male thread 25a of the X-axis fine control screw shaft 25. At one end of the outer slider 30, a side plate member 33 is fixed by a plurality of bolts 35, while the other end is mounted to the side plate 13 of the case 18 by a plurality of bolts 36. A first piston 37 is extending from the inner end of the side plate member 33, and a second piston 38 is extending from the inner end of the side plate 13.

Mounted centrally on the top surface of the inner slider is a central plate 40 so as to separate the top surface into two halves. A first hydraulic cylinder 41 and a second hydraulic cylinder 42 are mounted on the respective halves by cylinder fixing elements 44, 45 with their openings facing outwardly to the respective pistons 37, 38. Each hydraulic cylinder 41, 42 is provided at its outer periphery with a collar 41a, 42a for the abutting engagement with the cylinder fixing element 44, 45 and at its closed inner side with a hose coupling 41b, 42b for connecting one end of a hose 47, 48. The hose 47 as a first hose connects the first hydraulic cylinder 41 and an X-axis hydraulic cylinder 76 hereinafter described. The hose 48 as a second hose connects the second hydraulic cylinder 42 and an X-axis hydraulic cylinder 75 hereinafter described.

The piston 37 is inserted within the hydraulic cylinder 41 so as to provide an oil chamber 41', and the piston 38 is inserted within the hydraulic cylinder 42 so as to provide an oil chamber 42'.

The X-axis fine control mechanism 50 comprises the X-axis fine control handle 26, the X-axis fine control screw shaft 25, the bearing metal 21, the ring 22, the outer slider 30, the inner slider 31, the hydraulic cylinders 41, 42 and the pistons 37, 38.

In the X-axis fine control mechanism 50, the X-axis fine control screw shaft 25 is rotated when an operator moves the X-axis fine control handle 26. Since the fine control male thread 25a of the X-axis fine control screw shaft 25 is fixed to the inner slider 31, the volumes of the oil chambers 41', 42' are changed by the displacement of the inner slider 31 when the X-axis fine control handle 26 is rotated.

As shown in FIG. 2, the micromanipulator fine control unit 2 also includes a Y-axis fine control mechanism 51 for fore-and-aft movement and a Z-axis fine control mechanism 52 for up-and-down movement. The Y-axis fine control mechanism 51 and the Z-axis fine control mechanism 52 are substantially the same construction as the X-axis fine control mechanism 50. When the Y-axis fine control handle 54 is rotated, a non-shown inner slider fixed to a Y-axis fine control screw shaft (not shown) slides within a non-shown outer slider, thereby changing the volumes of a pair of oil chambers. These volume changes are transmitted to a pair of non-shown Y-axis hydraulic cylinders of the micromanipulator 3 through a pair of hoses 57, 58. When the Z-axis fine control handle 55 is rotated, a non-shown inner slider fixed to a Z-axis fine control screw shaft (not shown) slides within a non-shown outer slider, thereby changing the volumes of a pair of oil chambers. These volume changes are transmitted to a pair of non-shown Z-axis hydraulic cylinders through a pair of hoses 59, 60.

Figure 5:
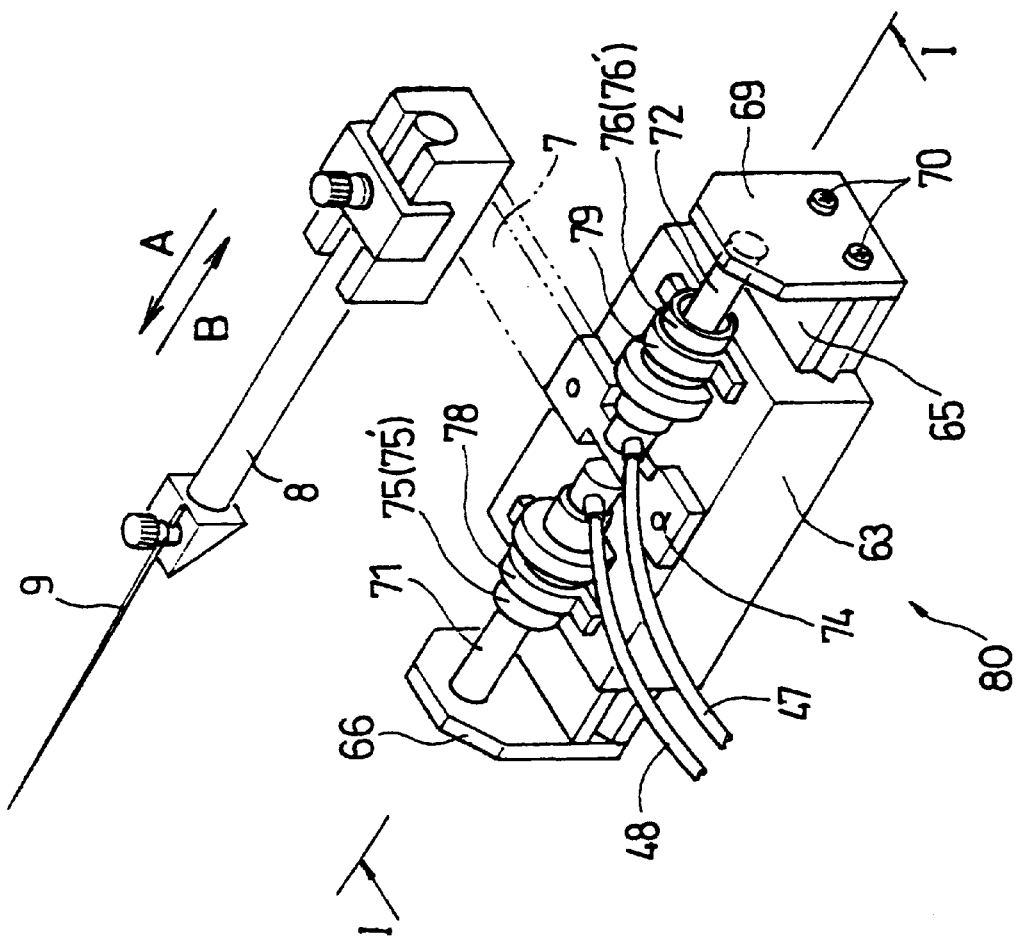
FIG. 5 is a perspective view showing an X-axis fine displacement mechanism of a micromanipulator according to first embodiment of the invention.
Figure 6:
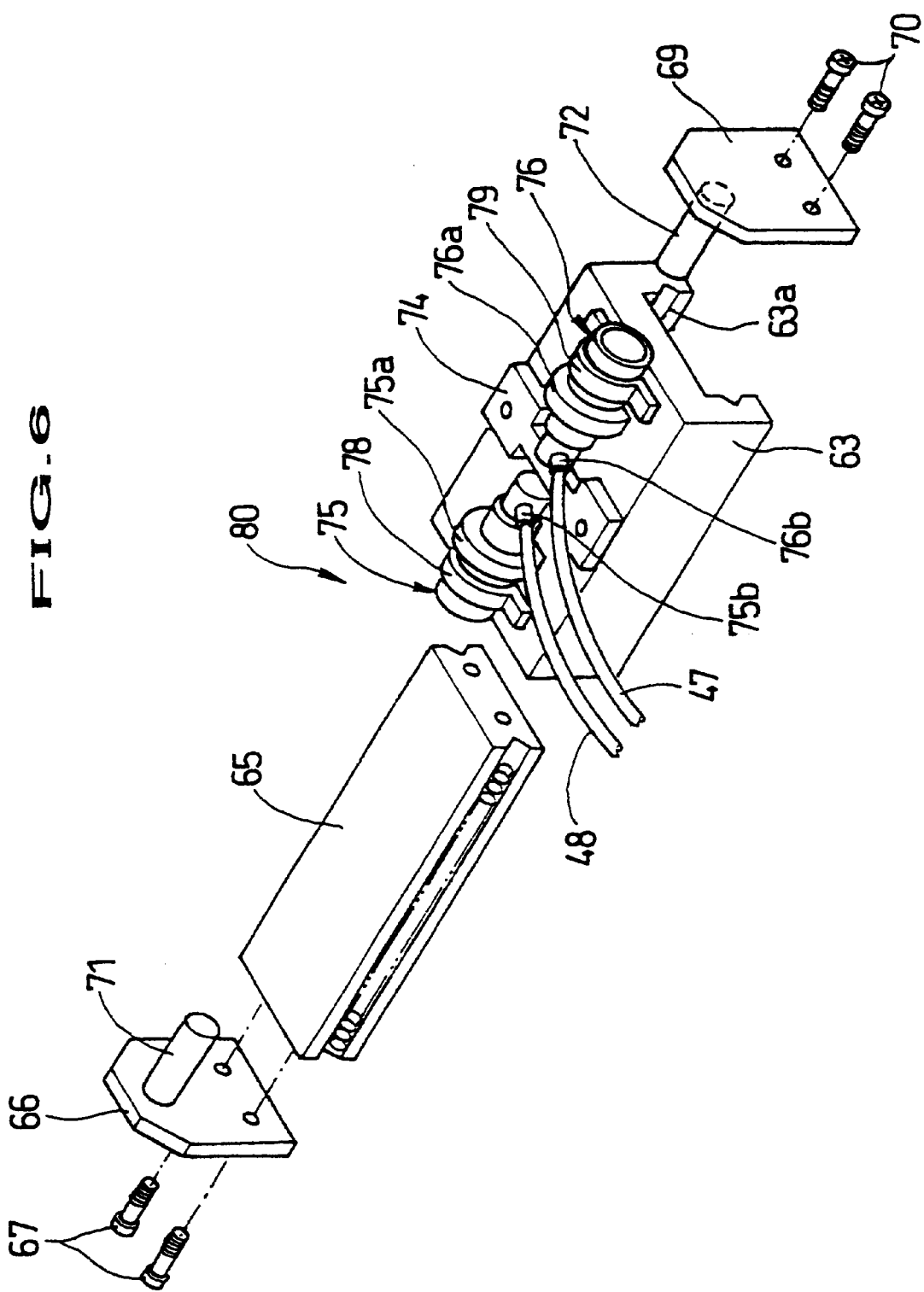
FIG. 6 is an exploded perspective view showing the X-axis fine displacement mechanism of FIG. 5.
Figure 7:
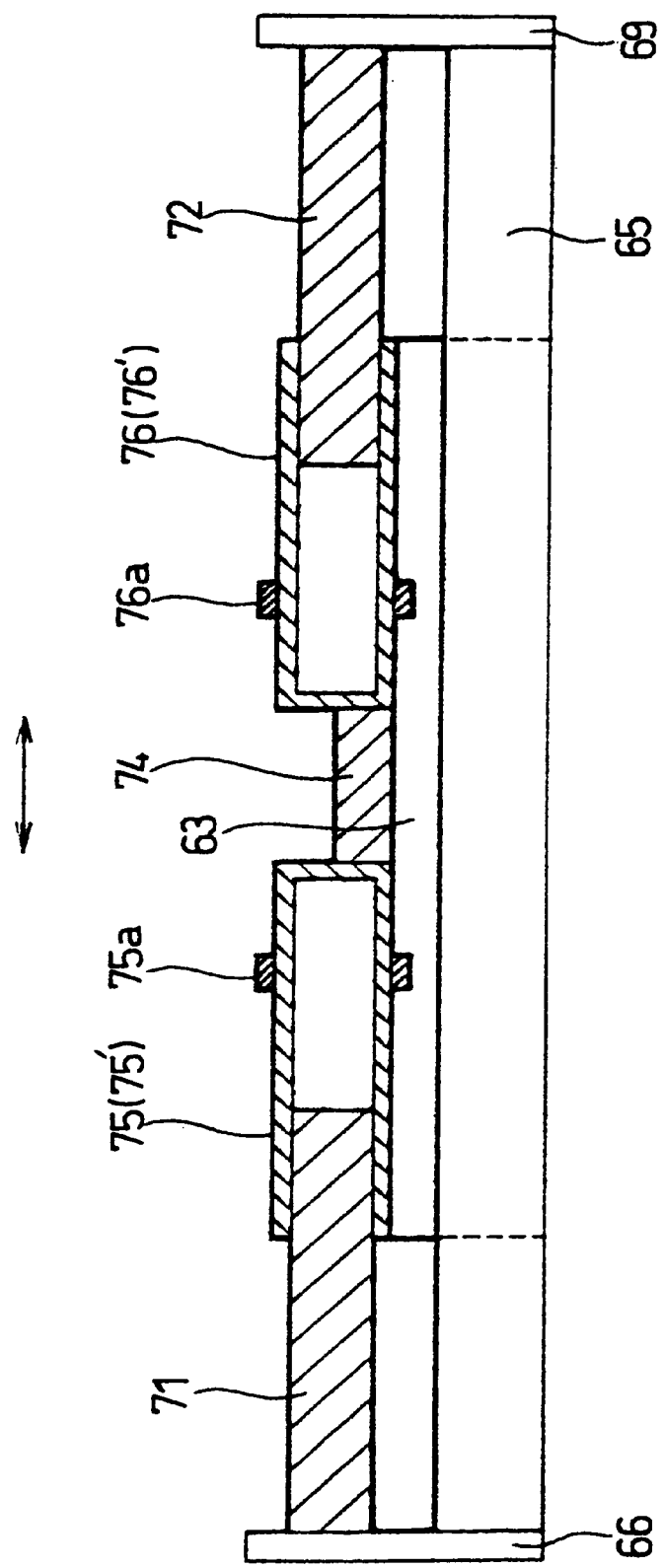
FIG. 7 is a sectional view taken along the line I—I of FIG. 5.

As shown in FIGS. 5 to 7, an X-axis fine displacement mechanism 80 of the micromanipulator 3 includes an X-axis outer slider 63 as a fine displacement member provided with a pair of inner guiding grooves 63a. An X-axis inner slider 65 is slidably mounted within the outer slider 63 through a non-shown linear-way bearing. The X-axis inner slider 65 is stationarily retained, while the X-axis outer slider 63 is slidable with respect to the X-axis inner slider 65.

At one end of the X-axis inner slider 65, a side plate member 66 is fixed by a plurality of bolts 67, while at the other end thereof, a side plate member 69 is fixed by a plurality of bolts 70. The side plate member 66 is provided with an inwardly extending fourth piston 71, and the side plate member 69 is provided with an inwardly extending third piston 72.

Mounted centrally on the top surface of the X-axis outer slider 63 is a central plate 74 so as to separate the top surface into two halves. An X-axis hydraulic cylinder 75 as a fourth hydraulic cylinder and an X-axis hydraulic cylinder 76 as a third hydraulic cylinder are mounted on the respective halves by cylinder fixing elements 78, 79 with their openings facing outwardly to the respective pistons 71, 72. Each X-axis hydraulic cylinder 75, 76 is provided at its outer periphery with a collar 75a, 76a for the abutting engagement with the cylinder fixing element 78, 79 and at its closed inner side with a hose coupling 75b, 76b for connecting the other end of the hose 48, 47.

The piston 71 is inserted within the X-axis hydraulic cylinder 75 so as to provide an oil chamber 75', and the piston 72 is inserted within the X-axis hydraulic cylinder 76 so as to provide an oil chamber 76'.

The X-axis fine displacement mechanism 80 comprises the hoses 47, 48, the X-axis outer slider 63, the X-axis inner slider 65, the X-axis hydraulic cylinders 75, 76 and the pistons 71, 72.

In this embodiment, the oil chamber 41' of the first hydraulic cylinder 41, the hose 47 and the oil chamber 76' of the X-axis hydraulic cylinder 76 provides a hydraulic closed circuit (hereinafter referred to as a first hydraulic closed circuit), while the oil chamber 42' of the second hydraulic cylinder 42, the hose 48 and the oil chamber 75' of the X-axis hydraulic cylinder 75 provides a hydraulic closed circuit (hereinafter referred to as a second hydraulic closed circuit). With the provision of such first and second hydraulic closed circuits, one hydraulic closed circuit functions as restricting means for restricting a volume change of the other closed circuit.

Referring to FIGS. 3 and 5, manner of operation of the hydraulically-operated micromanipulator apparatus will be described. Since the subject matter of the present invention is mainly related to drift-prevention, the mechanism thereof will be also described.

The first hydraulic closed circuit and the second hydraulic closed circuit include the oil chambers 41', 42' at the operating-side of the micromanipulator apparatus and the oil chambers 76', 75' at the actuating-side of the micromanipulator apparatus. When ambient temperature changes, hydraulic fluid in the respective chambers 41', 42', 76', 75' changes its volume. However, at the operating-side for example, the oil chambers 41', 42' are kept under the same condition, thereby the hydraulic fluid in one oil chamber causes the same expansion or contraction with the hydraulic fluid in the other oil chamber. In this embodiment, since the oil chambers 41', 42' are provided on the common inner slider 31 in opposing relation to each other, the volume change in one oil chamber is restricted by the hydraulic fluid in the other oil chamber. Such restriction occurs also to the actuating-side of the micromanipulator apparatus. Since the oil chambers 76', 75' are provided on the common X-axis outer slider 63 in opposing relation to each other, the volume change in one oil chamber is restricted by the hydraulic fluid in the other oil chamber. With such arrangement of the two hydraulic closed circuits, a volume change of hydraulic fluid is restricted, thereby drift of the microtool 9 fixed to the X-axis outer slider 63 can be prevented.

When operating the hydraulically-operated micromanipulator apparatus, an operator holds the knurled head of the X-axis fine control handle 26 provided at the micromanipulator fine control unit 2 and rotates it to the clockwise direction. The rotational movement of the knurled head is transmitted to the fine control male thread 25a of the X-axis fine control screw shaft 25. Since the fine control male thread 25a threadly engages with the internal thread 31a of the inner slider 31, the inner slider 31 is finely displaced by this rotation to the direction shown by the arrow A of FIG. 3. The hydraulic cylinders 41, 42 are also finely displaced by this rotation so that the oil chamber 41' becomes narrower and the oil chamber 42' becomes wider. When the volume of the oil chamber 41' is reduced, hydraulic fluid is flown out from the oil chamber 41'. The hydraulic fluid from the oil chamber 41' is then flown through the hose 47 into the oil chamber 76' of the X-axis hydraulic cylinder 76 against some resistance of the piston 72. Therefore, at the micromanipulator 3, the X-axis outer slider 63 of the X-axis fine displacement mechanism 80 is finely displaced toward the side plate member 66 (shown by the arrow A of FIG. 4). Since the microtool 9 is mounted on the X-axis outer slider 63 by the tightening device 7, the microtool 9 is finely displaced together with the X-axis outer slider 63. With the displacement of the X-axis outer slider 63, the volume of the oil chamber 75' is reduced and hydraulic fluid is flown out from the oil chamber 75'. The hydraulic fluid from the oil chamber 75' is then flown through the hose 48 into the increased oil chamber 42' of the X-axis fine control mechanism 50.

As described above, when the X-axis fine control handle 26 of the micromanipulator fine control unit 2 is rotated to move the inner slider 31 to the direction shown by the arrow A left-hand direction), the X-axis outer slider 63 of the micromanipulator 3 is moved to the direction shown by the arrow A (left-hand direction). In this operation, the first hydraulic closed circuit functions as part of the micromanipulator fine control unit and the hydraulically-operated micromanipulator, while the second hydraulic closed circuit functions as restricting means.

When the X-axis fine control handle 26 of the micromanipulator fine control unit 2 is rotated to move the inner slider 31 to the direction shown by the arrow B (right-hand direction), the hydraulic cylinders 41, 42 mounted on the inner slider 31 are moved to the direction shown by the arrow B. By this movement of the inner slider 31, the volume of the oil chamber 42' is reduced, while the volume of the oil chamber 41' is increased. Hydraulic fluid is then flown out from the reduced oil chamber 42' and it is flown through the hose 48 into the X-axis hydraulic cylinder 75 of the micromanipulator 3. The hydraulic fluid flown into the X-axis hydraulic cylinder 75 moves the X-axis outer slider 63 to the direction shown by the arrow B (right-hand direction), thereby narrowing the oil chamber 76' of the X-axis hydraulic cylinder 76. Hydraulic fluid is then flown out from the oil chamber 76' through the hose 47 into the hydraulic cylinder 41 of the micromanipulator fine control unit 2.

As described above, when the X-axis fine control handle 26 of the micromanipulator fine control unit 2 is rotated to move the inner slider 31 to the direction shown by the arrow B (right-hand direction), the X-axis outer slider 63 of the micromanipulator 3 is moved to the direction shown by the arrow B (right-hand direction). In this operation, the second hydraulic closed circuit functions as part of the micromanipulator fine control unit and the hydraulically-operated micromanipulator, while the first hydraulic closed circuit functions as restricting means.

Ratio of the volume of the oil chambers 41', 42' to that of the oil chambers 75', 76' may vary to be of 1:5 for example so as to ensure more precise operation of the micromanipulator.

As shown in FIG. 2, the Y-axis fine control mechanism 51 for fore-and-aft movement of the micromanipulator 3 and the Z-axis fine control mechanism 52 for up-and-down movement have substantially the same construction as the X-axis fine control mechanism 50. When the Y-axis fine control handle 54 of the micromanipulator fine control unit 2 is rotated, the micromanipulator 3 is moved to the Y-axis directions (fore-and-aft directions). Also, when the Z-axis fine control handle 55 of the micromanipulator fine control unit 2 is rotated, the micromanipulator 3 is moved to the Z-axis directions (up-and-down directions).

A mounting table 84 is attached to the X-axis outer slider 63. The mounting table 84 is provided with a non-shown V-shaped groove for inserting the base portion of the tightening device 7. The tightening device 7 is fixed to the mounting table 84 by a L-shaped fixing plate 85 and a fixing bolt 86. The tightening device 7, the holder 8 and the microtool 9 are finely movable in three dimensions by the X-axis fine displacement mechanism 80, the Y-axis fine control mechanism 81 and the Z-axis fine control mechanism 82.

Figure 8:
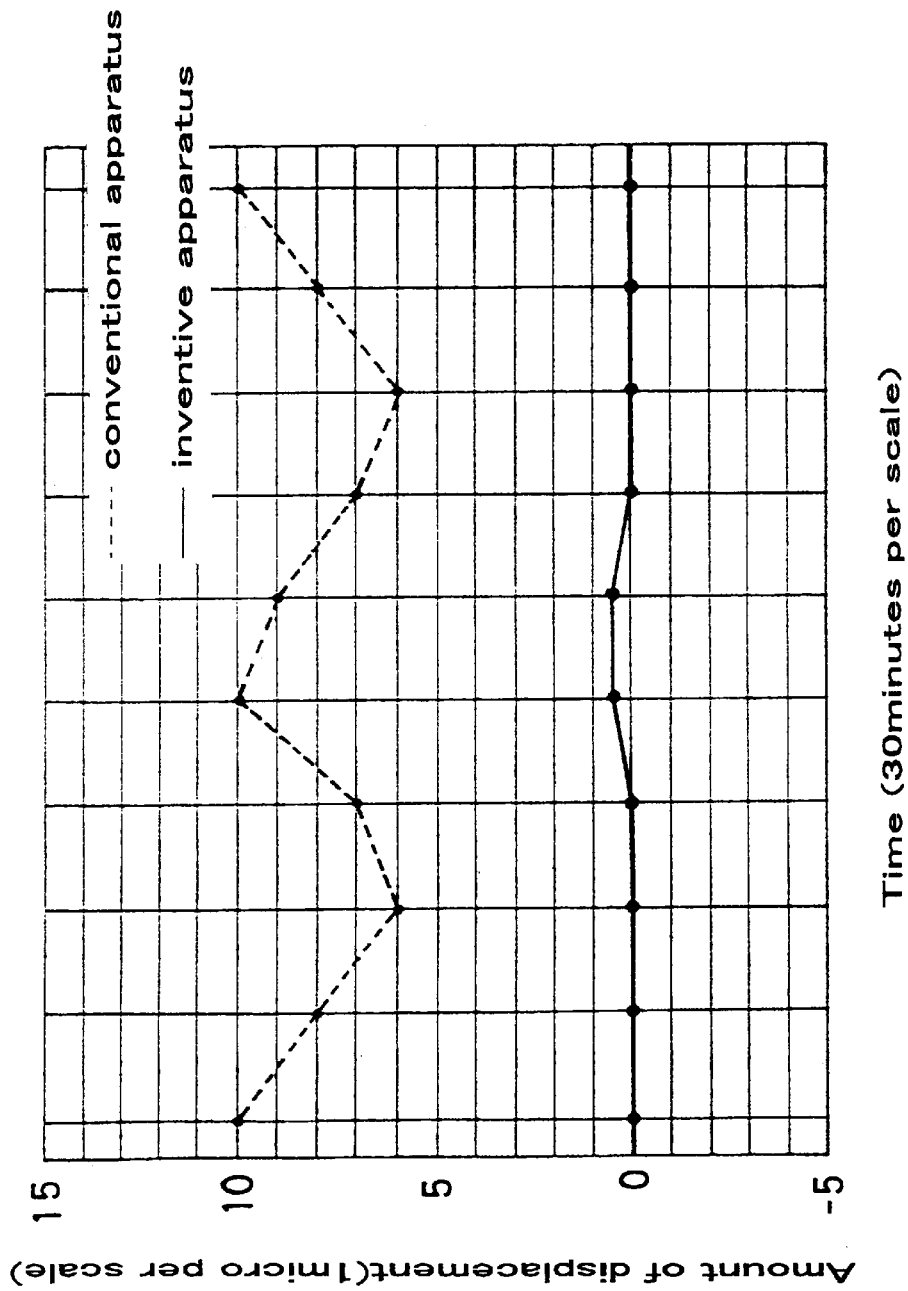
FIG. 8 is a table for the result of a comparative test, in which the relation between temperature change and amount of drift is shown for the inventive and a conventional hydraulically-operated micromanipulator apparatus.

Referring to FIG. 8, the result of a comparative test is shown. In this test, a conventional hydraulically-operated micromanipulator apparatus and the inventive hydraulically-operated micromanipulator apparatus are kept at a room temperature, the average temperature of 23° C. and the maximum temperature range of 8° C. around the average temperature. The table shows the relation between temperature change and amount of drift for each hydraulically-operated micromanipulator apparatus. In both conventional and inventive micromanipulator apparatus, the volume of the hydraulic cylinder (oil chamber) provided at the micromanipulator fine control unit to that of the hydraulic cylinder (oil chamber) provided at the hydraulically-operated micromanipulator is 1:5.

As a result, the inventive hydraulically-operated micromanipulator apparatus is not subject to drift. The micromanipulator apparatus according to the present invention therefore ensures precise and long-period operation.

It should be understood that the present invention is not limited by the above-described embodiment. Various modifications are possible within the scope of the claimed invention. For example, relative position between the hydraulic cylinders 41, 42 of the inner slider 31 and the pistons 37, 38 of the outer slider 30 may vary such that the hydraulic cylinders 41, 42 are mounted on the outer slider 30 of the micromanipulator fine control unit 2 and a common piston is mounted on the inner slider 31. Also, relative position between the X-axis hydraulic cylinders 75, 76 of the X-axis outer slider 63 and the pistons 71, 72 of the X-axis inner slider 65 may vary so that the X-axis hydraulic cylinders 75, 76 are mounted on the X-axis inner slider 65 of the micromanipulator 3 and a common piston is mounted on the X-axis outer slider 63.

Figure 9:
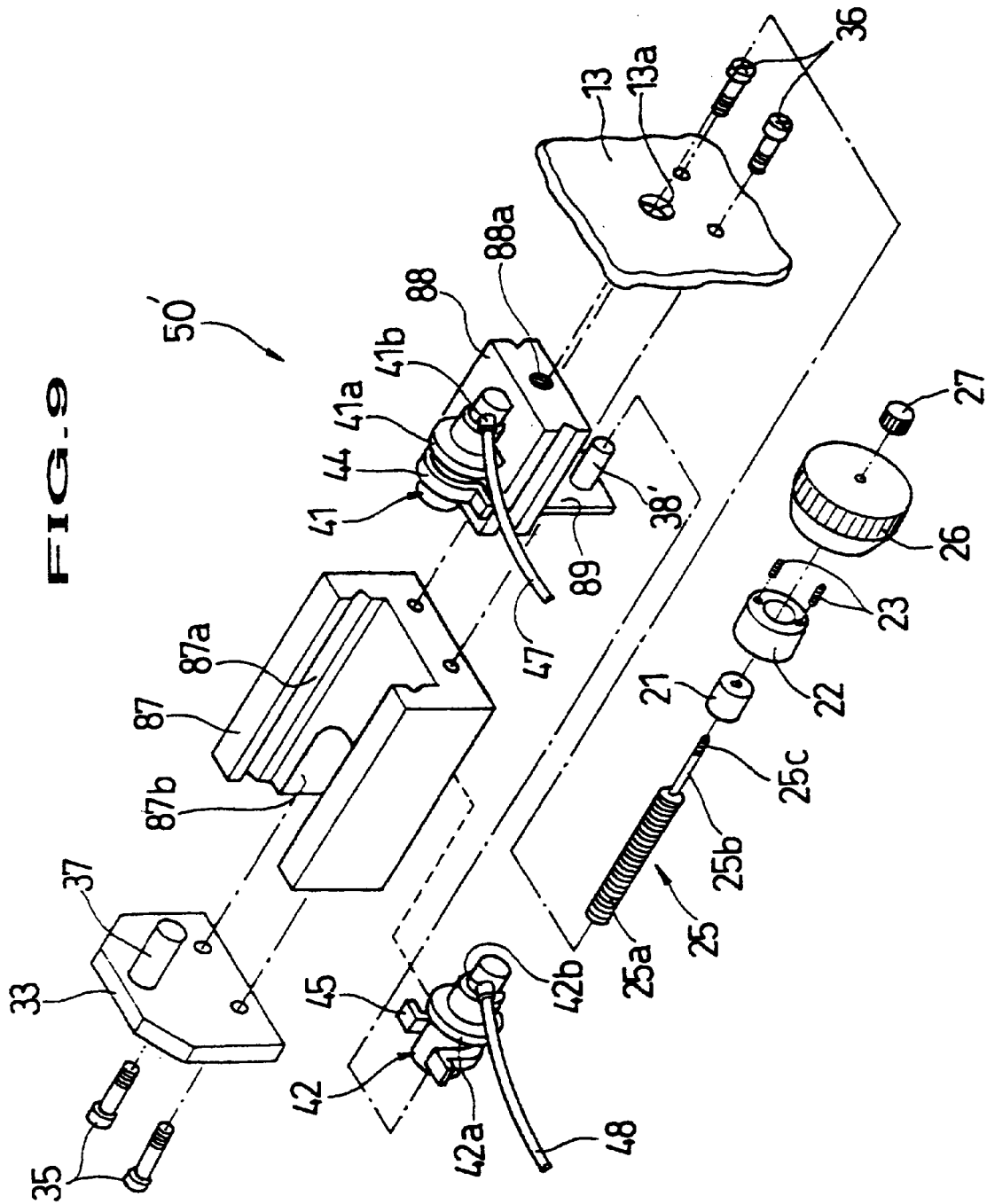
FIG. 9 is an exploded perspective view showing a modified embodiment of the X-axis fine control mechanism.

Referring now to FIG. 9, a modified embodiment of the hydraulically-operated micromanipulator apparatus is shown, in which the X-axis fine control mechanism 50' of the micromanipulator fine control unit includes an outer slider 87 as a basement. The outer slider 87 has a pair of guiding grooves 87a for receiving an inner slider 88 as a sliding table through a non-shown linearway bearing. The outer slider 87 also has an oblong cutout 87b at the bottom portion thereof. The inner slider 88 is provided at the tailing end with a threaded opening 88a for the engagement with the fine control male thread 25a of the X-axis fine control screw shaft 25. At the bottom surface of the inner slider 88, a piston fixing plate 89 extends downwardly through the oblong cutout 87b of the outer slider 87. The piston fixing plate 89 is provided with a second piston 38' horizontally extending toward the side plate 13. A first hydraulic cylinder 41 is mounted on the top surface of the inner slider 88 by a cylinder fixing element 44 with its opening facing to the side plate member 33. The first piston 37 of the side plate member 33 is fitted within the first hydraulic cylinder 41 so as to be movable to the fore-and-aft directions. At the bottom surface of the outer slider 87, a second hydraulic cylinder 42 is mounted by a cylinder fixing element 45 with its opening facing to the side plate member 33. The second piston 38' of the inner slider 88 is fitted within the second hydraulic cylinder 42 so as to be movable to the fore-and-aft directions. The hydraulically-operated micromanipulator apparatus also includes the Y-axis fine control mechanism (not shown) and the Z-axis fine control mechanism (not shown), which have substantially the same construction as the X-axis fine control mechanism 50'.

Figure 10:
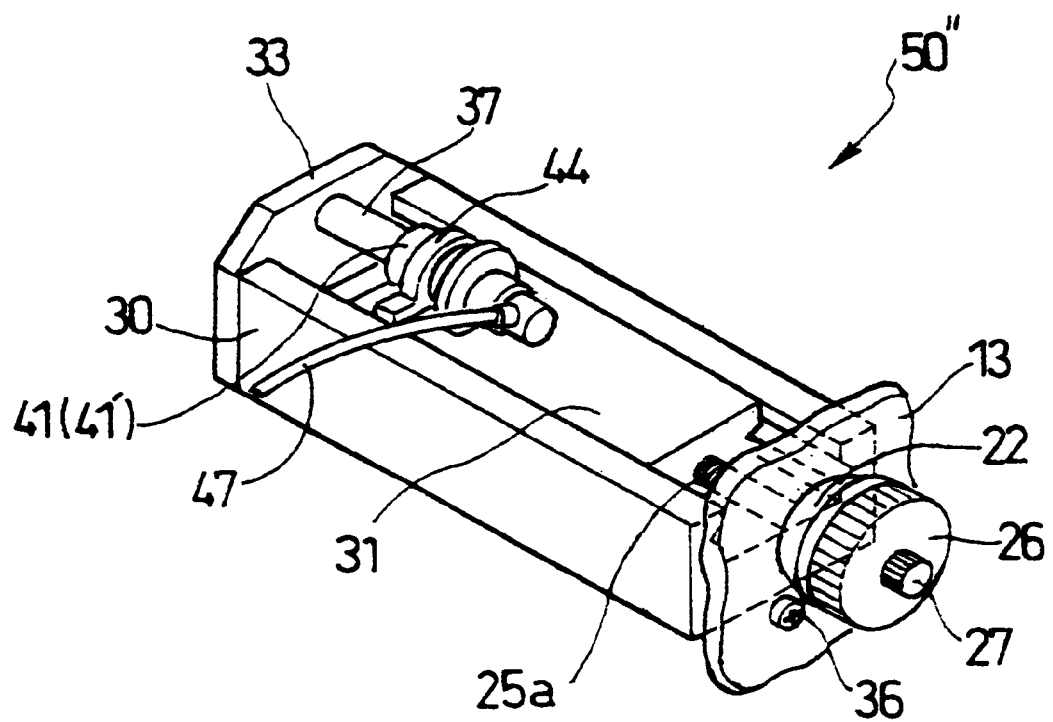
FIG. 10 is a perspective view showing a further modified embodiment of the X-axis fine control mechanism.
Figure 11:
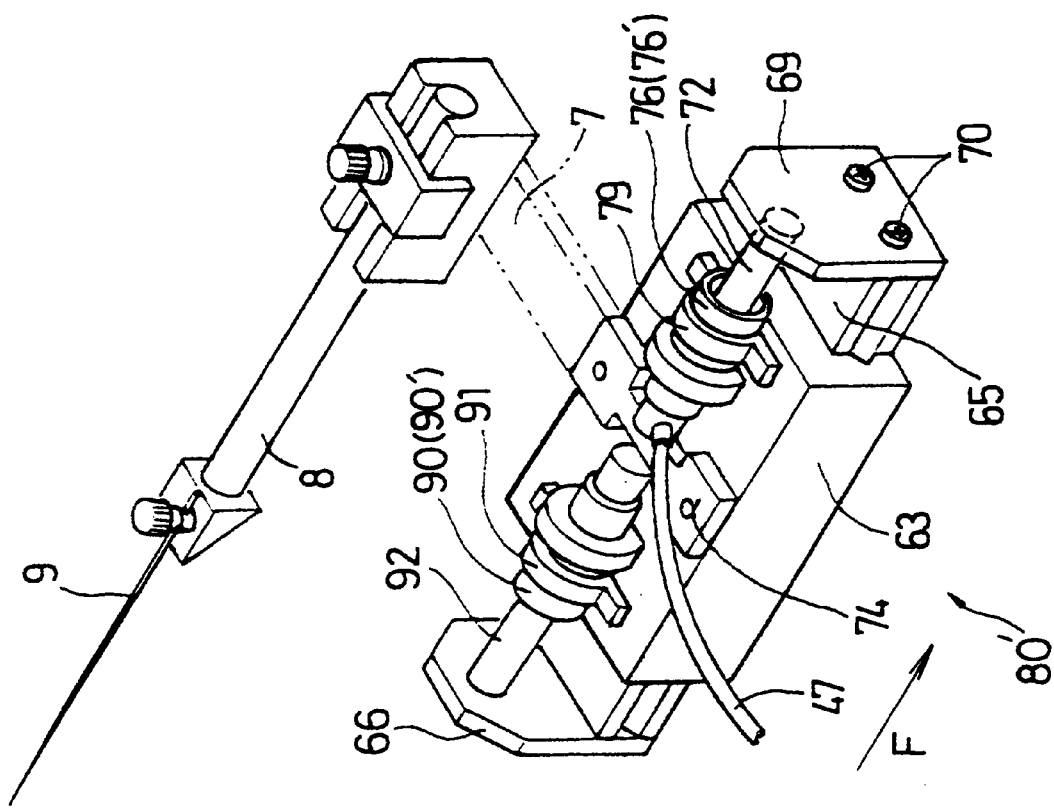
FIG. 11 is an exploded perspective view showing an X-axis fine displacement mechanism corresponding to the X-axis fine control mechanism of FIG. 10.

Referring now to FIGS. 10 and 11, a further modified embodiment of the hydraulically-operated micromanipulator apparatus is shown, in which restricting means is provided merely at the actuating-side of the micromanipulator apparatus. In this embodiment, the second hydraulic closed circuit is not provided. The X-axis fine displacement mechanism 80' includes a restricting hydraulic cylinder 90 and a non-shown spring for urging the X-axis outer slider 63 toward the side plate member 69 (shown by the arrow F). The restricting hydraulic cylinder 90 is mounted on the X-axis outer slider 63 by a cylinder fixing element 91 with its opening facing to the side plate member 66. The piston 92 of the side plate member 66 is fitted within the restricting hydraulic cylinder 90, thereby providing an oil chamber 90'. The restricting hydraulic cylinder 90 and the piston 92 are for applying a counterpressure to the X-axis outer slider 63 to be finely displaced by the increased hydraulic pressure within the X-axis hydraulic cylinder 76.

When the hydraulic pressure within the first hydraulic closed circuit, i.e. the closed circuit between the oil chamber 41' of the X-axis fine control mechanism 50" and the oil chamber 76' of the X-axis fine displacement mechanism 80' is increased due to an increased ambient temperature, the hydraulic pressure within the oil chamber 90' of the restricting hydraulic cylinder 90 is also increased, thereby applying a counterpressure to the X-axis outer slider 63. Increment of the volume within the oil chamber 76' is therefore restricted. Meanwhile, when the hydraulic pressure within the first hydraulic closed circuit is reduced, the hydraulic pressure within the oil chamber 90' of the restricting hydraulic cylinder 90 is also reduced, thereby restricting the volume change within the oil chamber 76'. As a result, drift of the X-axis outer slider 63 and hence drift of the microtool 9 attached thereto can be prevented.

Manner of operation of this hydraulically-operated micromanipulator apparatus will now be described. When an operator holds the knurled head of the X-axis fine control handle 26 and rotates it to the clockwise direction, the inner slider 31 is finely displaced toward the side plate member 33. The hydraulic cylinder 41 is also finely displaced by this rotational movement of the knurled head so that the oil chamber 41' becomes narrower. When the volume of the oil chamber 41' is reduced, hydraulic fluid is flown out from the oil chamber 41'. The hydraulic fluid from the oil chamber 41' is then flown through the hose 47 into the oil chamber 76' of the X-axis hydraulic cylinder 76 against some resistance of the non-shown spring. Therefore, at the micromanipulator 3, the X-axis outer slider 63 of the X-axis fine displacement mechanism 80' is finely displaced toward the side plate member 66.

When the operator rotates the knurled head of the X-axis fine control handle 26 to the counterclockwise direction, the inner slider 31 is finely displaced toward the side plate 13. The hydraulic cylinder 41 is also finely displaced by this rotational movement of the knurled head so that the oil chamber 41' becomes wider. By this movement of the hydraulic cylinder 41, the hydraulic pressure within the X-axis hydraulic cylinder 76 is reduced. Since the X-axis outer slider 63 of the X-axis fine displacement mechanism 80' is urged by the non-shown spring toward the side plate member 69, the X-axis hydraulic cylinder 76 is finely displaced toward the side plate member 69. Hydraulic fluid within the X-axis hydraulic cylinder 76 is then flown into the oil chamber 41' of the hydraulic cylinder 41.

It should be understood that the above modification may of course be applied to the other Y-axis fine control mechanism or Z-axis fine control mechanism. In this embodiment, since the second hydraulic closed circuit is not required for each micromanipulator fine control unit, only three hoses 47, 57, 59 are necessary for the hydraulically-operated micromanipulator apparatus.

In the above-mentioned modified embodiments, restricting means for restricting a volume change of each oil chamber is described as compensating means. However, other compensating means may be employed such that a volume change of hydraulic fluid itself is allowed and the amount of displacement due to this volume change can be compensated. For example, a compensating unit is provided between the operating-side piston and the fine displacement member. The compensating unit includes a hydraulic cylinder and a piston such that when the volume of hydraulic fluid is increased or reduced, the distance between the hydraulic cylinder and the piston is reduced or increased.

The ratio of the hydraulic cylinders of the micromanipulator fine control unit to the hydraulic cylinders of the micromanipulator is not limited to 1:1 or 1:5, other ratios may of course be employed. Such ratio may vary by changing the volume of each oil chamber.

Above hydraulically-operated micromanipulator apparatus are described for three-axes movement. However, the present invention can be applied to a hydraulically-operated micromanipulator apparatus of single axis or two-axes control.

Figure 12:
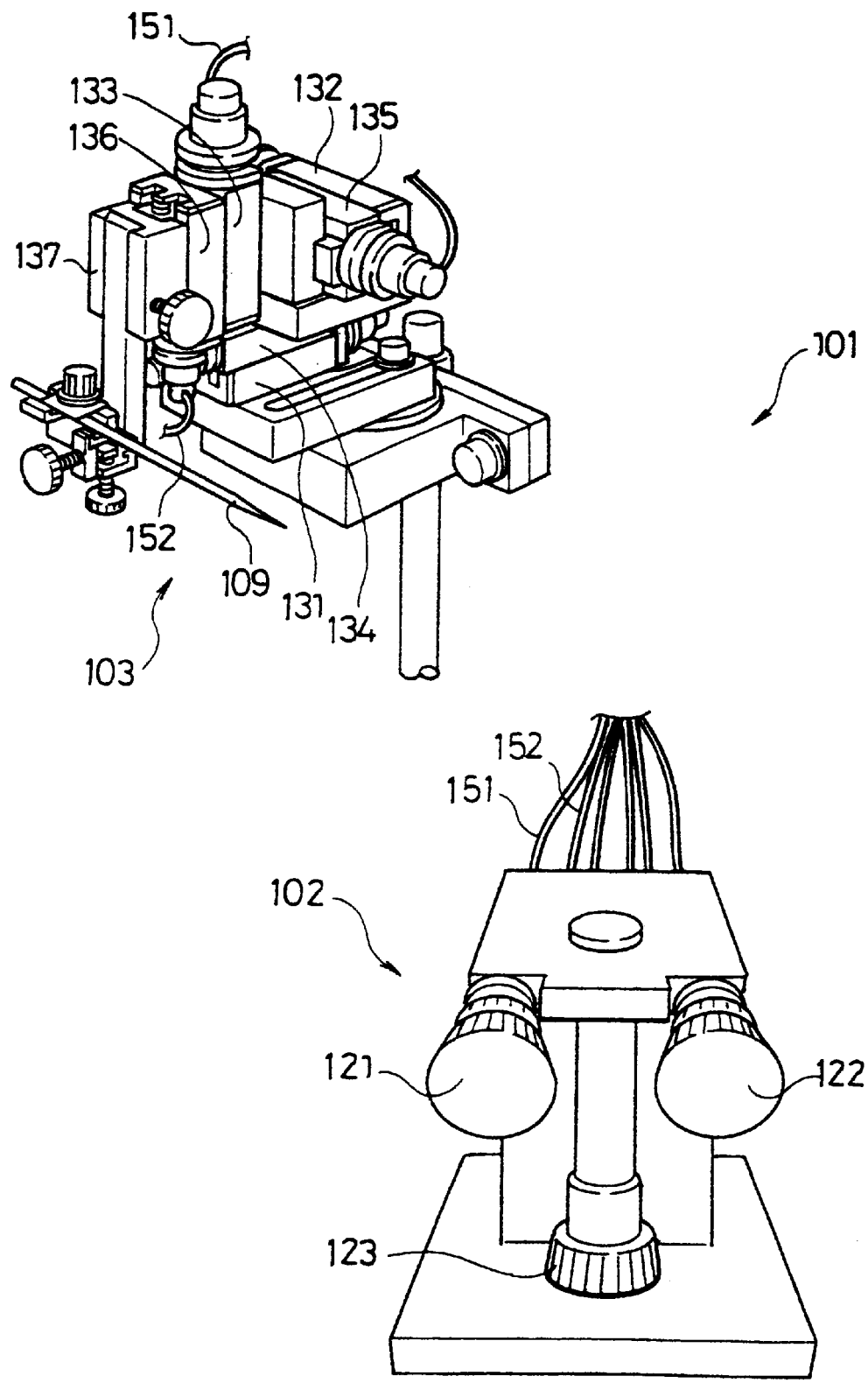
FIG. 12 is a perspective view showing a second embodiment of a hydraulically-operated micromanipulator apparatus according to the present invention.

A second embodiment of a hydraulically-operated micromanipulator apparatus according to the present invention will be described with reference to FIGS. 12 to 16. Referring particular to FIG. 12, the hydraulically-operated micromanipulator apparatus 101 comprises an operating unit 102 and an actuating unit 103.

Figure 13A:
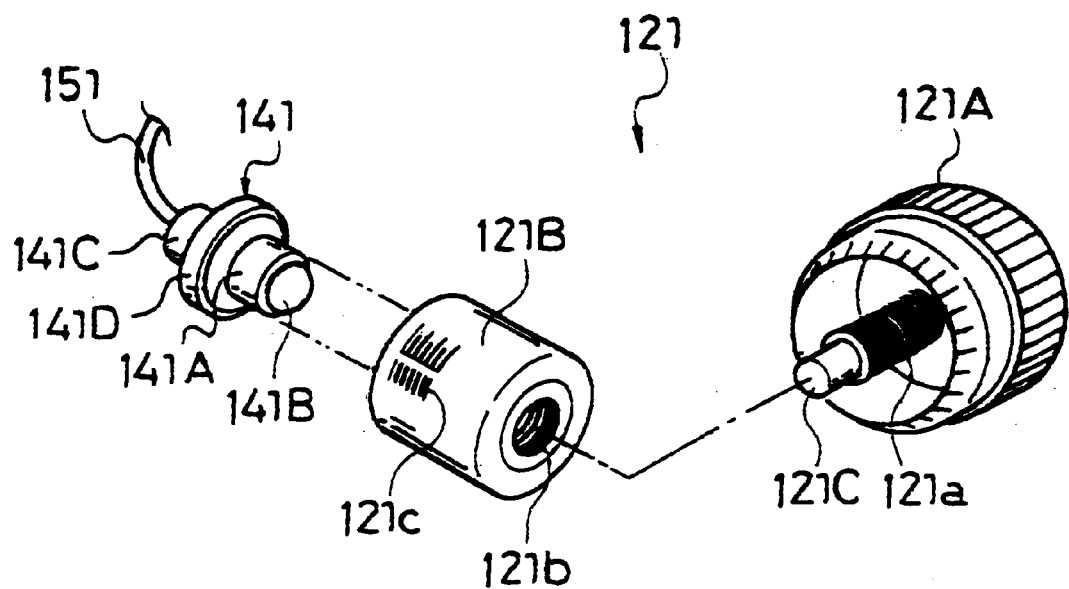
FIG. 13 is an exploded perspective view schematically showing an operating unit of the hydraulically-operated micromanipulator apparatus of FIG. 12.
Figure 13B:
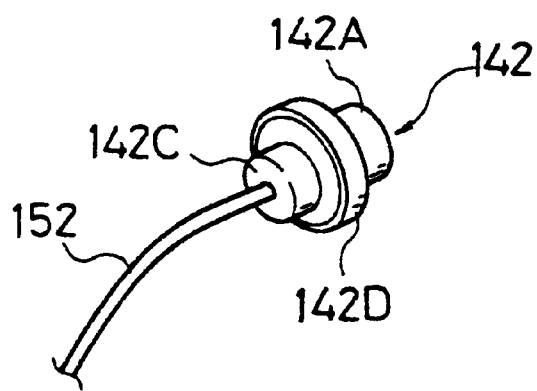

The operating unit 102 includes a Z-axis dial 121, an X-axis dial 122 and a Y-axis dial 123 as fine control means for the respective Z, X, Y axes control. As shown in FIG. 13(*a*), the Z-axis dial 121 comprises a control handle 121A and a bearing 121B. The control handle 121A is provided with a male thread portion 121*a*. A tubular push portion 121C is further provided at the front end of the male thread portion 121*a*.

The bearing 121B is provided with an internal thread portion 121*b* for the engagement with the male thread portion 121*a* of the control handle 121A Provided outer periphery of the bearing 121B is a scale mark 121*c* for the reference of a fine control operation. A hydraulic oil chamber 141 as an operating-side fluid chamber is positioned at one end of the bearing 121B remote from the control handle 121A. The hydraulic oil chamber 141 comprises a steel-made tubular member 141A having an open end and a sealing member 141B for covering the open end. The sealing member 141B is made of a flexible material such as rubber. The hydraulic oil chamber 141 is mounted to the bearing 121B with the tubular member 141A fitted within the bearing 121B so that the sealing member 141B and the push portion 121C face to each other.

The tubular member 141A is provided wit h a hose coupling 141C at the other end opposite to the open end. A hose 151 is connected to the hose coupling 141C so that the hydraulic oil chamber 141 is in communication with the hose 151. When the control handle 121A is rotated, the push portion 121C is moved to the forward or rearward direction, thereby changing the volume of the hydraulic oil chamber 141. A collar 141D is provided at the outer periphery of the tubular member 141A.

As shown in FIG. 13(*b*), the operating unit 102 also includes a compensating fluid chamber 142 to be filled with drift-compensation fluid. The compensating fluid chamber 142 is formed by a steel-made tubular member 142A. A hose coupling 142C is provided at one end of the compensating fluid chamber 142. A hose 152 is connected to the hose coupling 142C so that the compensating fluid chamber 142 is i n communication with the hose 152. A collar 142A is provided at the outer periphery of the tubular member 142A. The volume and the length of the hose 151 are substantially the same as those of the hose 152.

As shown in FIG. 12, the actuating unit 103 includes an X-axis slider 131, a Y-axis slider 132 and a Z-axis slider 133 for the respective X, Y, Z axes movement. These sliders 131, 132, 133 are respectively mounted with an X-axis drift-prevention slider 134, a Y-axis drift-prevention slider 135 and a Z-axis drift-prevention slider 136. Constructions of the Z-axis slider 133 and the Z-axis drift-prevention slider 136 are particularly described below since the other X-axis and Y-axis sliders 131, 132, and X-axis and Y-axis drift-prevention sliders 134, 135 are substantially the same as these sliders 133, 136.

Figure 14:
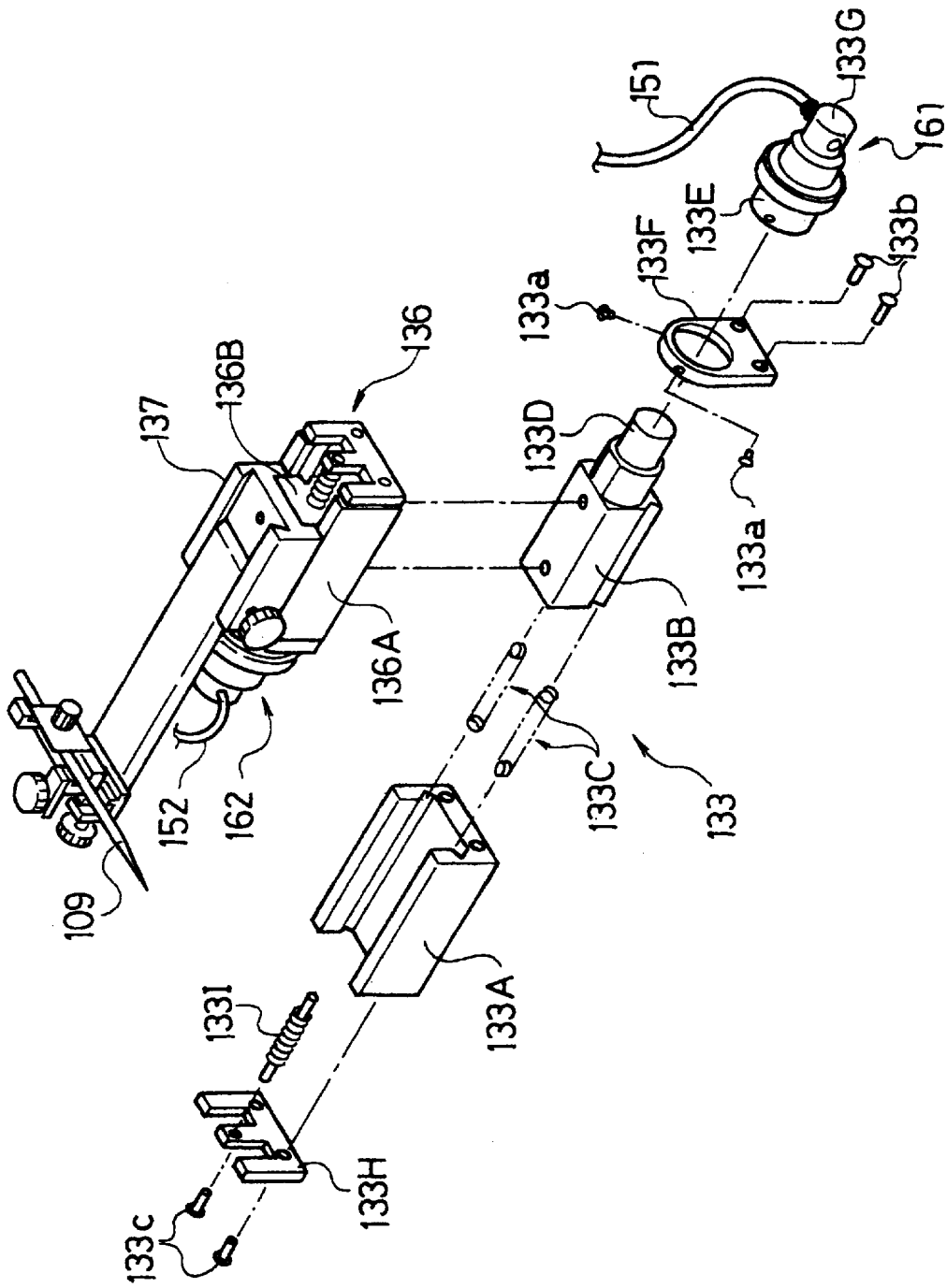
FIG. 14 is an exploded perspective view showing a Z-axis slider of the hydraulically-operated micromanipulator apparatus of FIG. 12.

As shown in FIG. 14, the Z-axis slider 133 includes an outer slider 133A for receiving therein an inner slider 133B through a linear-way bearing 133C. The inner slider 133B is provided at one end with a piston 133D, which is movable within a cylinder portion 133E, thereby providing a hydraulic oil chamber 161 as an actuating-side fluid chamber. The cylinder portion 133E is provided with a hose coupling 133G so that the hose 151 connected thereto is in communication with the hydraulic oil chamber 161. The hydraulic oil chamber 161 and the hydraulic oil chamber 141 at the operating unit 102 connected through the hose 151 are filled with hydraulic fluid.

The cylinder portion 133E is fitted within a through opening of a side plate member 133F and is fixed to the side plate member 133F by a plurality of bolts 133*a*. The side plate member 133F is mounted at one end of the outer slider 133A by a plurality of bolts 133*b*. At the other end of the outer slider 133A, a side plate member 133H is mounted by a plurality of bolts 133*c*. A spring 1331 is positioned between the side plate member 133H and the inner slider 133B, thereby urging the inner slider 133B toward the cylinder portion 133E.

The Z-axis drift-prevention slider 136 has substantially the same construction as the Z-axis slider 133. As shown in FIG. 14, the outer slider 136A of the Z-axis drift-prevention slider 136 is fixed to the inner slider 133B of the Z-axis slider 133. The compensating fluid chamber 162 of the Z-axis drift-prevention slider 136 is filled with drift-prevention fluid, and the volume thereof is substantially the same as that of the hydraulic oil chamber 161 at the Z-axis slider 133. The hydraulic oil chamber 161 and the compensating fluid chamber 162 are positioned in opposing relation to each other along the Z-axis through the Z-axis slider 133 and the Z-axis drift-prevention slider 136. The drift-prevention fluid to be filled within the compensating fluid chamber 162 is the same as the hydraulic fluid within the hydraulic oil chamber 161. A microtool fixing member 137 is attached to the inner slider 136B of the Z-axis drift-prevention slider 136 for supporting a microtool 109, such as a glass electrode.

Figure 15:
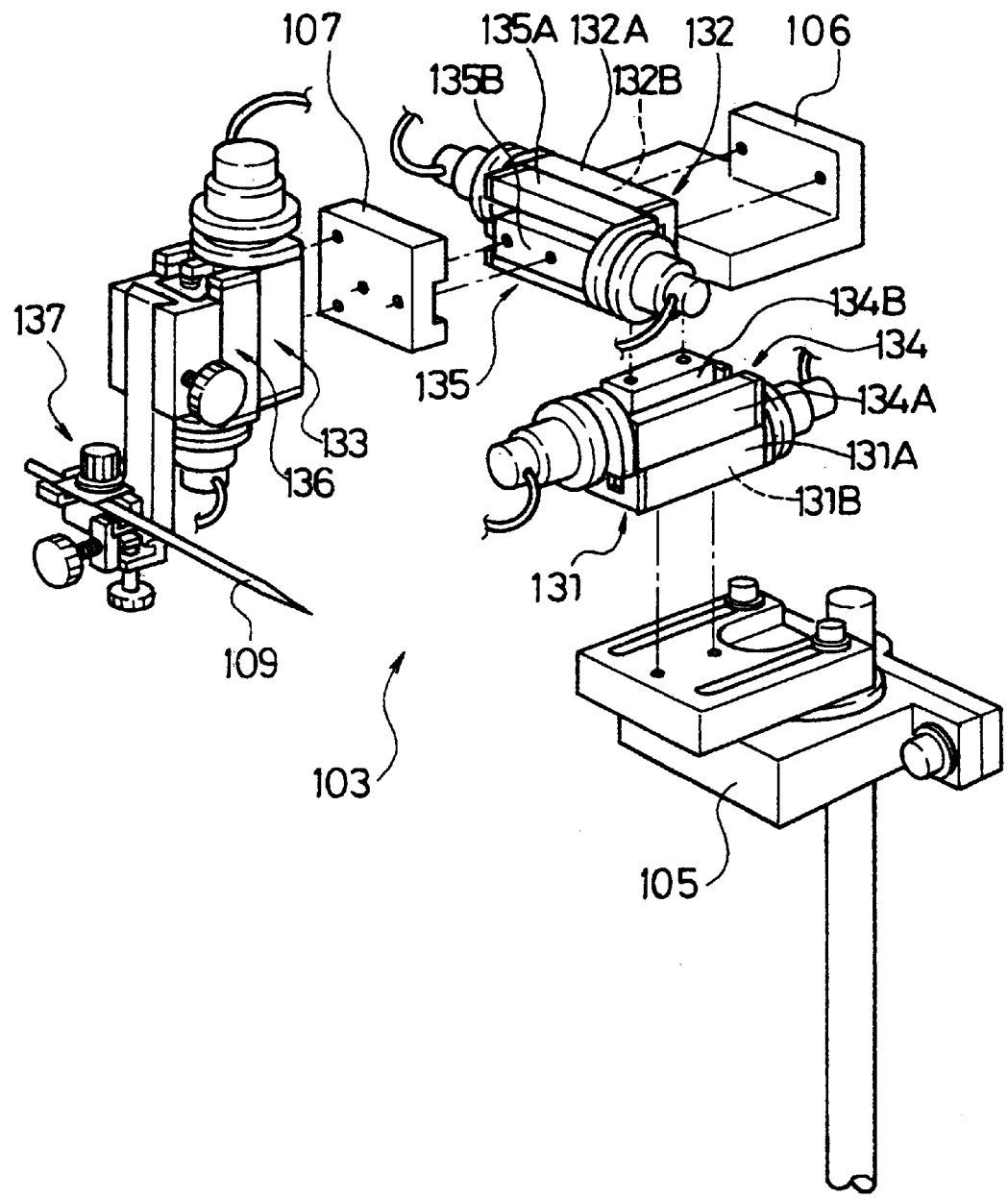
FIG. 15 is an exploded perspective view showing an actuating unit of the hydraulically-operated micromanipulator apparatus of FIG. 12.

As shown in FIG. 15, the inner slider 131B of the X-axis slider 131 is fixed to the outer slider 134A of the X-axis drift-prevention slider 134. Also, the inner slider 132B of the Y-axis slider 132 is fixed to the outer slider 135A of the Y-axis drift-prevention slider 135. The outer slider 131A of the X-axis slider 131 is fixed to the basement 105, and the inner slider 134B of the X-axis drift-prevention slider 134 is fixed to the outer slider 132A of the Y-axis slider 132 through an angle bar 106. The inner slider 135B of the Y-axis drift-prevention slider 135 is also fixed to the outer slider 133A of the Z-axis slider 133 through a fixing element 107. By this arrangement, the microtool fixing member 137 attached to the inner slider 136B of the Z-axis drift-prevention slider 136 can be movable in three dimensions, i.e. fore-and-aft, up-and-down and right-and-left directions.

Manner of operation of this hydraulically-operated micromanipulator apparatus will now be described with reference to FIGS. 12 to 15.

When rotating the Z-axis dial 121 to the clockwise direction, the push portion 121C presses the sealing member 141B, thereby narrowing the hydraulic oil chamber 141. When the volume of the hydraulic oil chamber 141 is reduced, hydraulic fluid is flown out from the hydraulic oil chamber 141. The hydraulic fluid from the hydraulic oil chamber 141 is then flown through the hose 151 into the hydraulic oil chamber 161 of the Z-axis slider 133, thereby the inner slider 133B is displaced toward the side plate member 133H against the urging force of the spring 133I. Since the outer slider 136A of the Z-axis drift-prevention slider 136 is fixed to the inner slider 133B, the Z-axis drift-prevention slider 136 is also displaced toward the side plate member 133H. Therefore, the microtool fixing member 137 and the microtool 109 attached thereto are displaced together with the inner slider 133B of the Z-axis slider 133.

When rotating the Z-axis dial 121 to the counterclockwise direction, the push portion 121C moves away from the sealing member 141B. Since the hydraulic pressure within the hydraulic oil chamber 161 is reduced, the inner slider 133B of the Z-axis slider 133 is moved toward the side plate member 133F by the urging force of the spring 133I. Hydraulic fluid within the hydraulic oil chamber 161 is then flown through the hose 151 into hydraulic oil chamber 141 of the operating unit 102. Since the relative position between the outer slider 136A and the inner slider 136B of the Z-axis drift-prevention slider 136 is not changed, the microtool fixing member 137 and the microtool 109 attached thereto are displaced together with the inner slider 133B of the Z-axis slider 133.

Control of the X-axis or the Y-axis movement is carried out by the substantially same operation as the above-described Z-axis movement.

Figure 16:
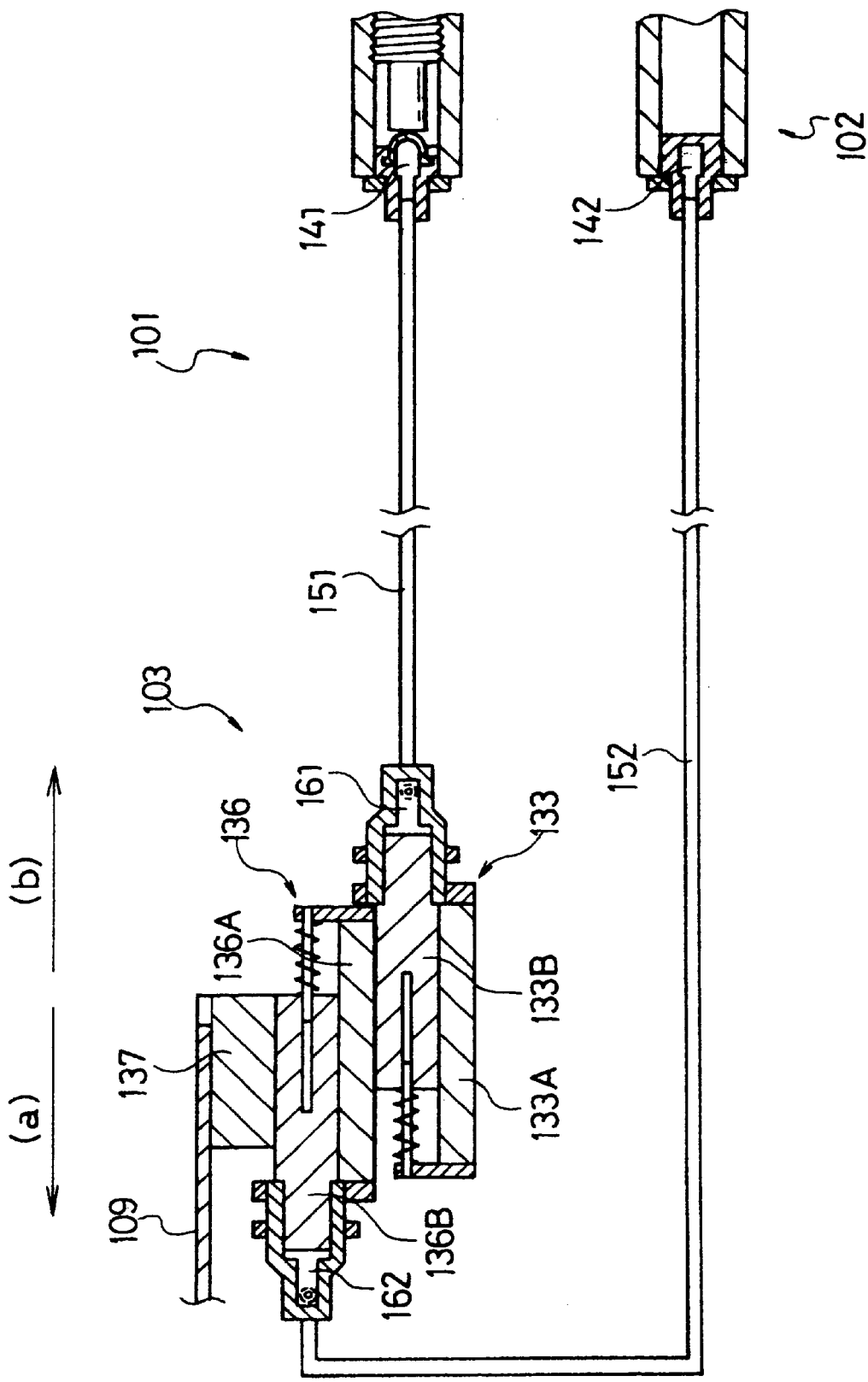
FIG. 16 is an explanatory view showing a drift-prevention mechanism of the hydraulically-operated micromanipulator apparatus of FIG. 12.

Drift-prevention mechanism will now be described with reference to FIG. 16. The volume of the hydraulic oil chamber 141 at the operating unit 102 is the same as that of the compensating fluid chamber 142, while the volume of the hydraulic oil chamber 161 at the actuating unit 103 is the same as that of the compensating fluid chamber 162. The hose 151 and the hose 152 are the same in length and volume. Therefore, the amount of the hydraulic fluid within the hydraulic oil chambers 141 and 161 connected by the hose 151 is the same as that of the hydraulic fluid within the compensating fluid chambers 142 and 162 connected by the hose 152. Here, definition of the term "same" includes minor tolerance to the extent that the relative position of the microtool 109 is substantially unchanged when the volume of hydraulic fluid is changed.

When ambient temperature changes, for example rising, both hydraulic fluid and drift-prevention fluid within the hydraulically-operated micromanipulator apparatus 101 expand. By such expansion of the hydraulic fluid, the volume of the hydraulic oil chamber 161 is increased, and the inner slider 133B of the Z-axis slider 133 is displaced to the direction shown by the arrow (a) since the outer slider 133A of the Z-axis slider 133 is stationarily retained. Meanwhile, the volume of the drift-prevention fluid is also increased to the same amount with the hydraulic fluid since the drift-prevention fluid is subject to such increased temperature as well. The volume of the compensating fluid chamber 142 is constant, therefore, when the drift-prevention fluid expands, the volume of the compensating fluid chamber 162 is increased, thereby displacing the inner slider 136B of the Z-axis drift-prevention slider 136 to the direction shown by the arrow (b).

In this embodiment, the inner slider 133B of the Z-axis slider 133 is fixed to the outer slider 136A of the Z-axis drift-prevention slider 136. As a result, since the outer slider 133A is stationary, the inner slider 133B and the outer slider 136A are displaced to the direction shown by the arrow (a), while the inner slider 136B is displaced to the direction shown by the arrow (b). The relative position between the outer slider 133A of the Z-axis slider 133 and the inner slider 136B of the Z-axis drift-prevention slider 136 is not changed. Therefore, drift of the microtool 109 due to a temperature change can be prevented.

Contrary to the above, when ambient temperature falls, the volumes of the hydraulic fluid and the drift-prevention fluid are both reduced. The inner slider 133B of the Z-axis slider 133 is then displaced to the direction shown by the arrow (b) since the outer slider 133A of the Z-axis slider 133 is stationarily retained. Meanwhile, the inner slider 136B of the Z-axis drift-prevention slider 136 is displaced to the direction shown by the arrow (a). The relative position between the outer slider 133A of the Z-axis slider 133 and the inner slider 136B of the Z-axis drift-prevention slider 136 is not changed.

The X-axis slider 131 and the X-axis drift-prevention slider 134 are substantially the same as the Z-axis slider 133 and the Z-axis drift-prevention slider 136. Also, the Y-axis slider 132 and the Y-axis drift-prevention slider 135 are substantially the same construction as the Z-axis slider 133 and the Z-axis drift-prevention slider 136. Therefore, drift of the microtool 109 can be prevented for the X-axis and the Y-axis directions as well.

In the above embodiment, the volume of the hydraulic oil chamber 141 at the operating unit 102 is the same as that of the hydraulic oil chamber 161 at the actuating unit 103, and the volume of the compensating fluid chamber 142 at the operating unit 102 is the same as that of the compensating fluid chamber 162 at the actuating unit 103. However, the ratio may vary as long as the relative position between the outer slider 133A of the Z-axis slider 133 and the inner slider 136B of the Z-axis drift-prevention slider 136 is kept unchanged when ambient temperature changes. For example, the ratio of the chambers at the operating unit 102 to the chambers at the actuating unit 103 may be 1:5 for facilitating precise fine control of the microtool 109.

The above hydraulically-operated micromanipulator apparatus 101 is described for three-axes movement. However, the present invention can be applied to a hydraulically-operated micromanipulator apparatus of single axis or two-axes control.

Further, in stead of providing two compensating fluid chambers at the operating unit and the actuating unit, respectively, only one compensating fluid chamber can be employed at the actuating unit.

A third embodiment of a hydraulically-operated micromanipulator apparatus according to the present invention will be described below with reference to FIGS. 17 to 22.

Figure 17:
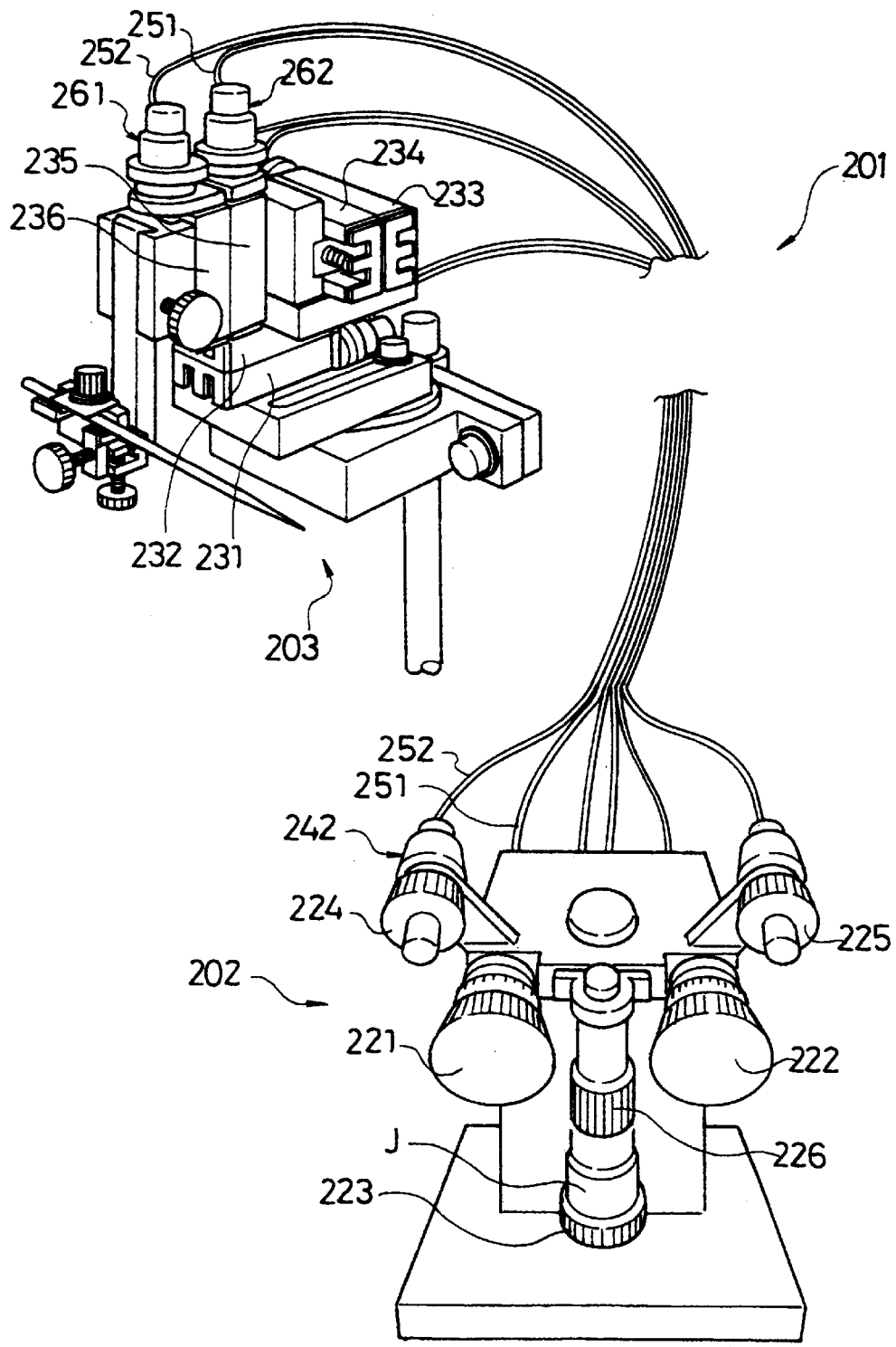
FIG. 17 is a perspective view showing a third embodiment of a hydraulically-operated micromanipulator apparatus according to the present invention.

Referring particular to FIG. 17, the hydraulically-operated micromanipulator apparatus 201 comprises an operating unit 202 and an actuating unit 203.

Figure 18A:
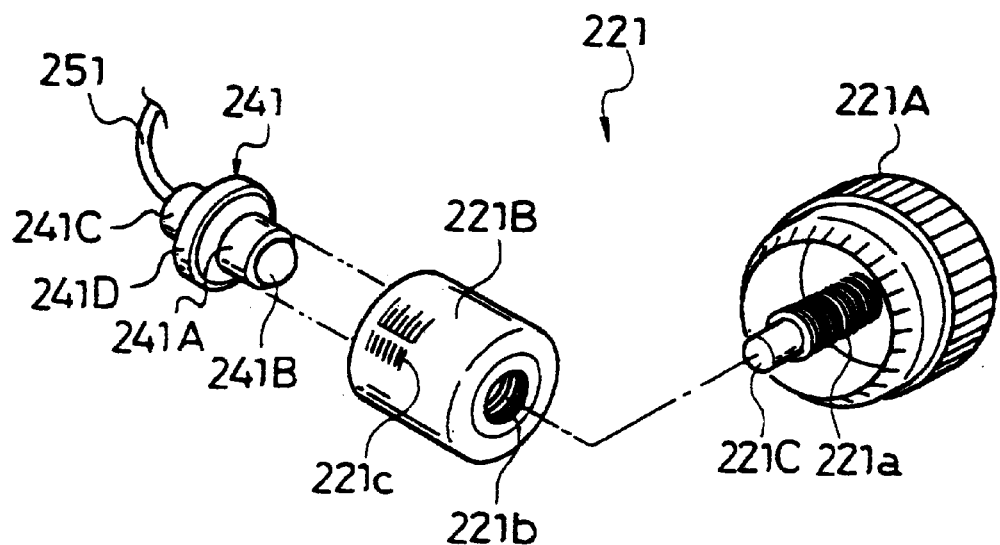
FIG. 18 is an exploded perspective view schematically showing an operating unit of the hydraulically-operated micromanipulator apparatus of FIG. 17.

The operating unit 202 includes a Z-axis fine control dial 221, an X-axis fine control dial 222 and a Y-axis fine control dial 223 as fine control means for the respective Z, X, Y axes control, and also a Z-axis coarse control dial 224, an X-axis coarse control dial 225 and a Y-axis coarse control dial 226 as coarse control means for the respective Z, X, Y axes control. As shown in FIG. 18(a), the Z-axis fine control dial 221 comprises a control handle 221A and a bearing 221B. The control handle 221A is provided with a male thread portion 221a. A tubular push portion 221C is further provided-at the front end of the male thread portion 221a.

The bearing 221B is provided with an internal thread portion 221b for the engagement with the male thread portion 221a of the control handle 221A. Provided outer periphery of the bearing 221B is a scale mark 221c for the reference of a fine control operation. A first hydraulic oil chamber 241 as an operating-side first hydraulic fluid chamber is positioned at one end of the bearing 221B remote from the control handle 221A. The first hydraulic oil chamber 241 comprises a steel-made tubular member 241A having an open end and a sealing member 241B for covering the open end. The sealing member 241B is made of a flexible material such as rubber. The first hydraulic oil chamber 241 is mounted to the bearing 221B with the tubular member 241A fitted within the bearing 221B so that the sealing member 241B and the push portion 221C face to each other.

The tubular member 241A is provided with a hose coupling 241C at the other end opposite to the open end. A hose 251 is connected to the hose coupling 241C so that the first hydraulic oil chamber 241 is in communication with the hose 251. When the control handle 221A is rotated, the push portion 221C is moved to the forward or rearward direction, thereby changing the volume of the first hydraulic oil chamber 241. A collar 241D is provided at the outer periphery of the tubular member 241A.

Figure 18B:
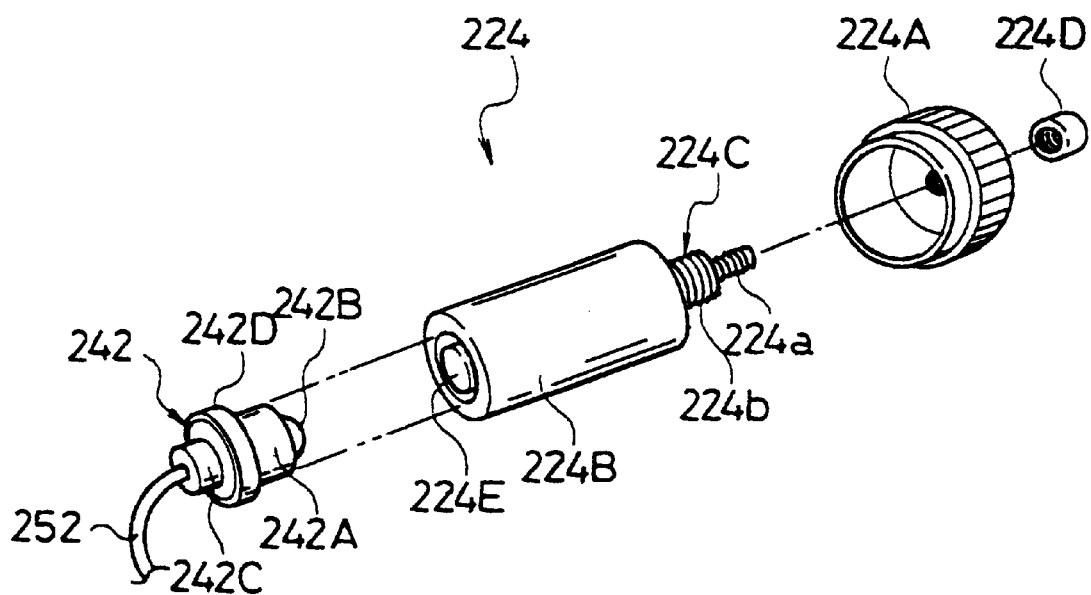

As shown in FIG. 18(b), the Z-axis coarse control dial 224 comprises a control handle 224A and a bearing 224B. The bearing 224B is provided with an internal thread portion (not shown) for the engagement with a threaded shaft 224C. The threaded shaft 224C is provided at one end with a front stem portion 224a having reduced diameter, and at the other end with a push portion 224E. The control handle 224A threadly engages with the front stem portion 224a of the threaded shaft 224C, and further a fixing nut 224d is mounted on the control handle 224A so that the threaded shaft 224C is rotated together with the control handle 224A. A second hydraulic oil chamber 242 as an operating-side second hydraulic fluid chamber is positioned in opposing relation to the control handle 224A. The second hydraulic oil chamber 242 comprises a steel-made tubular member 242A having an open end and a sealing member 242B for covering the open end. The sealing member 242B is made of a flexible material such as rubber. The second hydraulic oil chamber 242 is mounted to the bearing 224B with the tubular member 242A fitted within the bearing 224B so that the sealing member 242B and the push portion 224E face to each other.

The tubular member 242A is provided with a hose coupling 242C at the other end opposite to the open end. A hose 252 is connected to the hose coupling 242C so that the second hydraulic oil chamber 242 is in communication with the hose 252. A collar 242D is provided at the outer periphery of the tubular member 242A. The volume of the second hydraulic oil chamber 241 is the same as that of the first hydraulic oil chamber 241.

By this arrangement, when the control handle 224A is rotated, the push portion 224E is moved to the forward or rearward direction, thereby changing the volume of the second hydraulic oil chamber 242. The amount of displacement of the push portion 224E when rotating the control handle 22A is greater than that of the push portion 221C when rotating the control handle 221A.

An X-axis fine control dial 222 and an X-axis coarse control dial 225 are provided for changing the volumes of an X-axis first hydraulic oil chamber and an X-axis second hydraulic oil chamber, respectively. Also, a Y-axis fine control dial 223 and a Y-axis coarse control dial 226 are provided for changing the volumes of a Y-axis first hydraulic oil chamber and a Y-axis second hydraulic oil chamber, respectively. These fine control dials 222, 223 and coarse control dials 225, 226 are the same as the Z-axis fine control dial 221 and the Z-axis coarse control dial 224. In this embodiment, a joystick J is further provided for X-Y directional control.

As shown in FIG. 17, the actuating unit 203 includes an X-axis first slider 231, an X-axis second slider 232, a Y-axis first slider 233, a Y-axis second slider 234, a Z-axis first slider 235 and a Z-axis second slider 236 for the respective X, Y, Z axes movement. Construction of the Z-axis second slider 236 is particularly described below since these sliders have substantially the same construction.

Figure 19:
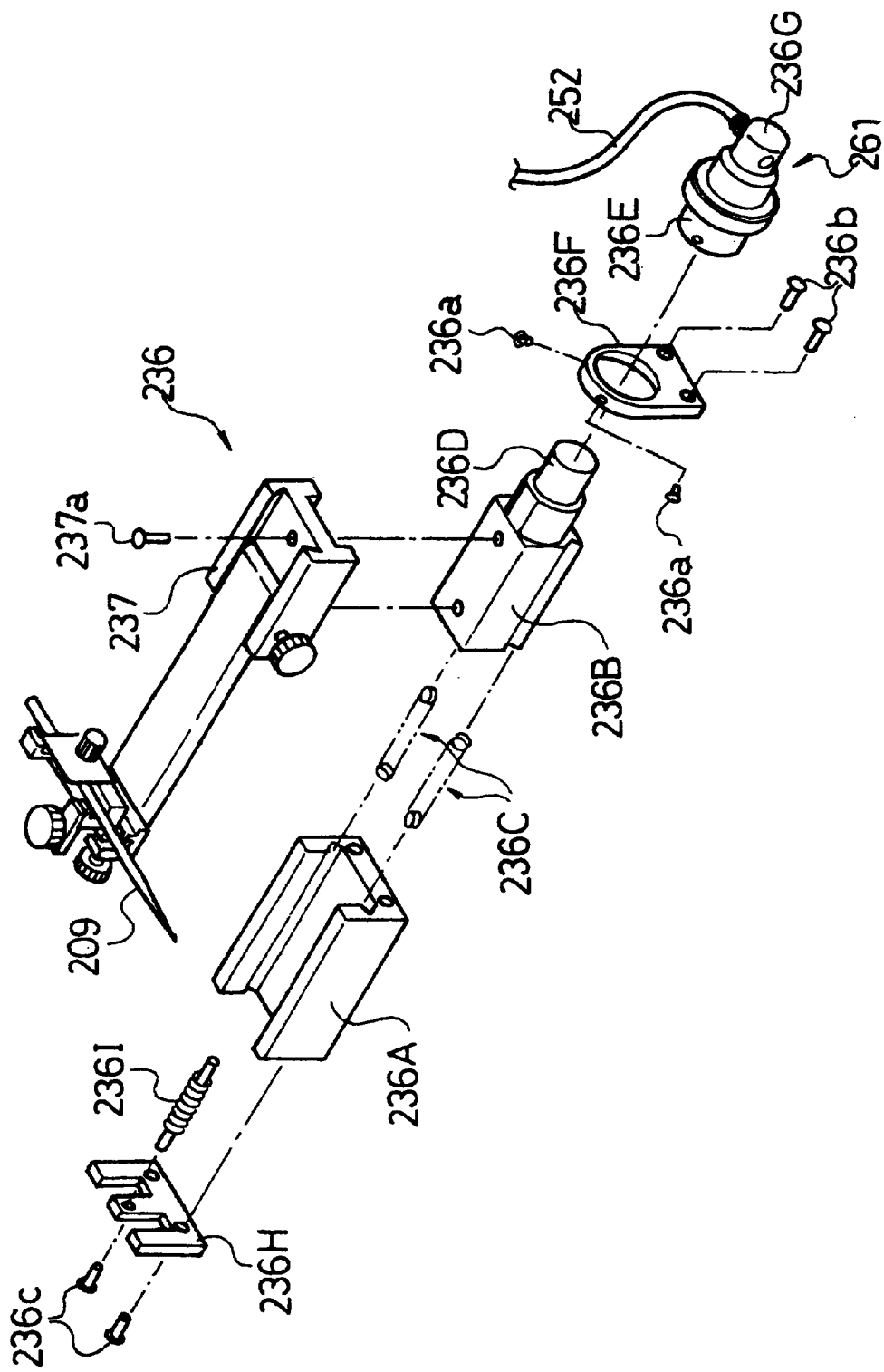
FIG. 19 is an exploded perspective view showing a Z-axis second slider of the hydraulically-operated micromanipulator apparatus of FIG. 17.

As shown in FIG. 19, the Z-axis second slider 236 includes an outer slider 236A for receiving therein an inner slider 236B as a second sliding member through a linear-way bearing 236C. The inner slider 236B is provided at one end with a piston 236D, which is movable within a cylinder portion 236E, thereby providing a second hydraulic oil chamber 261 as an actuating-side second hydraulic fluid chamber.

The cylinder portion 236E is provided with a hose coupling 236G so that the hose 252 connected thereto is in communication with the second hydraulic oil chamber 261. The second hydraulic oil chamber 261 and the second hydraulic oil chamber 241 at the operating unit 202 connected through the hose 252 are filled with hydraulic fluid.

The cylinder portion 236E is fitted within a through opening of a side plate member 236F and is fixed to the side plate member 236F by a plurality of bolts 236a. The side plate member 236F is mounted at one end of the outer slider 236A by a plurality of bolts 236b. At the other end of the outer slider 236A, a side plate member 236H is mounted by a plurality of bolts 236c. A spring 2361 is positioned between the side plate member 236H and the inner slider 236B, thereby urging the inner slider 236B toward the cylinder portion 236E. A microtool fixing member 237 is attached to the inner slider 236B by a bolt 237a for supporting a microtool 209, such as a glass electrode.

Figure 20:
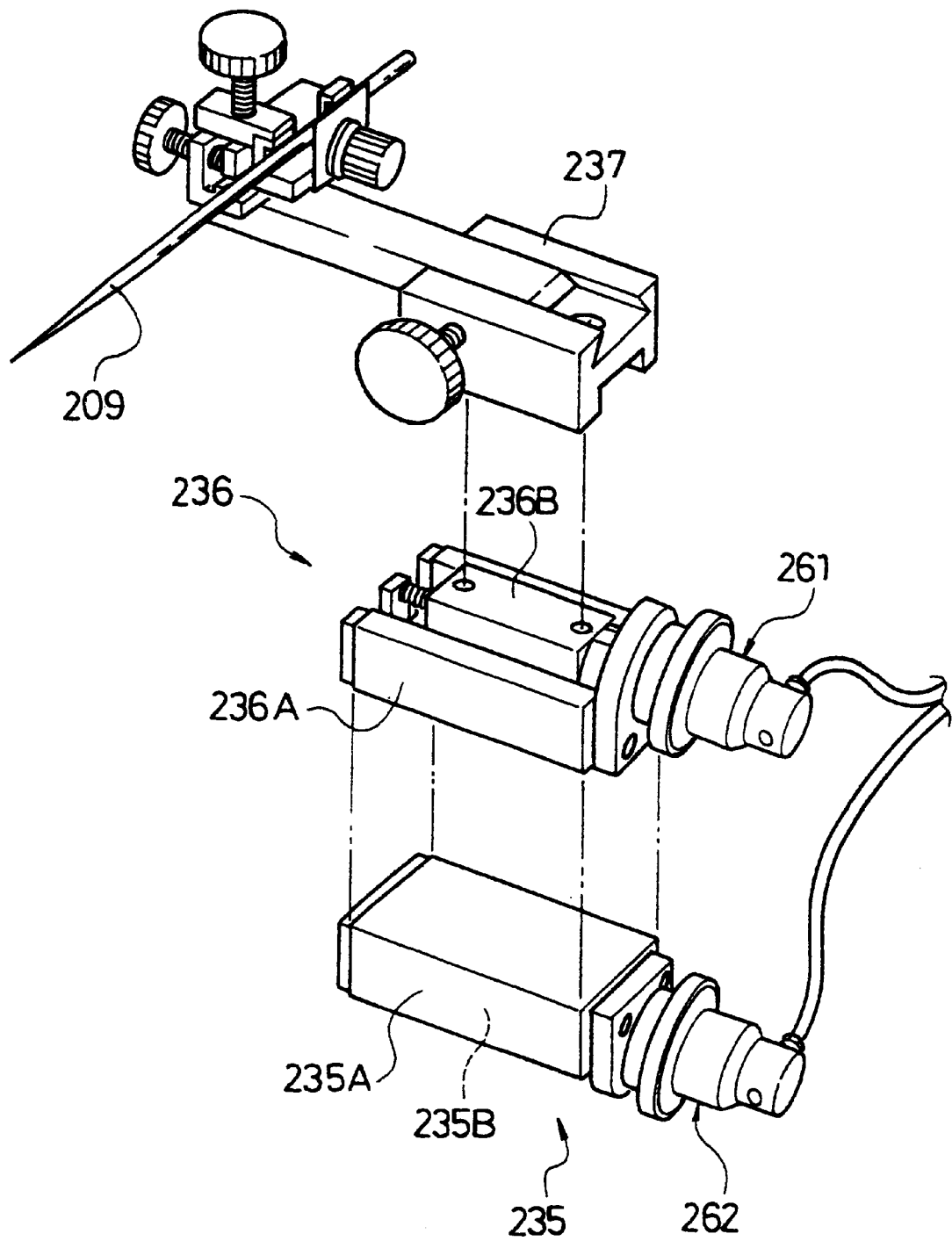
FIG. 20 is an exploded perspective view schematically showing an actuating unit of the hydraulically-operated micromanipulator apparatus of FIG. 17.

As shown in FIG. 20, the Z-axis first slider 235 has the same construction as the Z-axis second slider 236. The outer slider 236A of the Z-axis second slider 236 is fixed to the outer slider 235A of the Z-axis first slider 235. A first sliding member according to the invention is formed by these fixed outer sliders 236A, 236B. A first hydraulic oil chamber 262 as an actuatingside first hydraulic fluid chamber is formed to have the same volume with the second hydraulic oil chamber 261 of the Z-axis second slider 236. The first hydraulic oil chamber 262 is connected with the first hydraulic oil chamber 241 through the hose 251 (referring to FIG. 18). The inner slider 235B of the Z-axis first slider 235 is stationarily retained.

Figure 21:
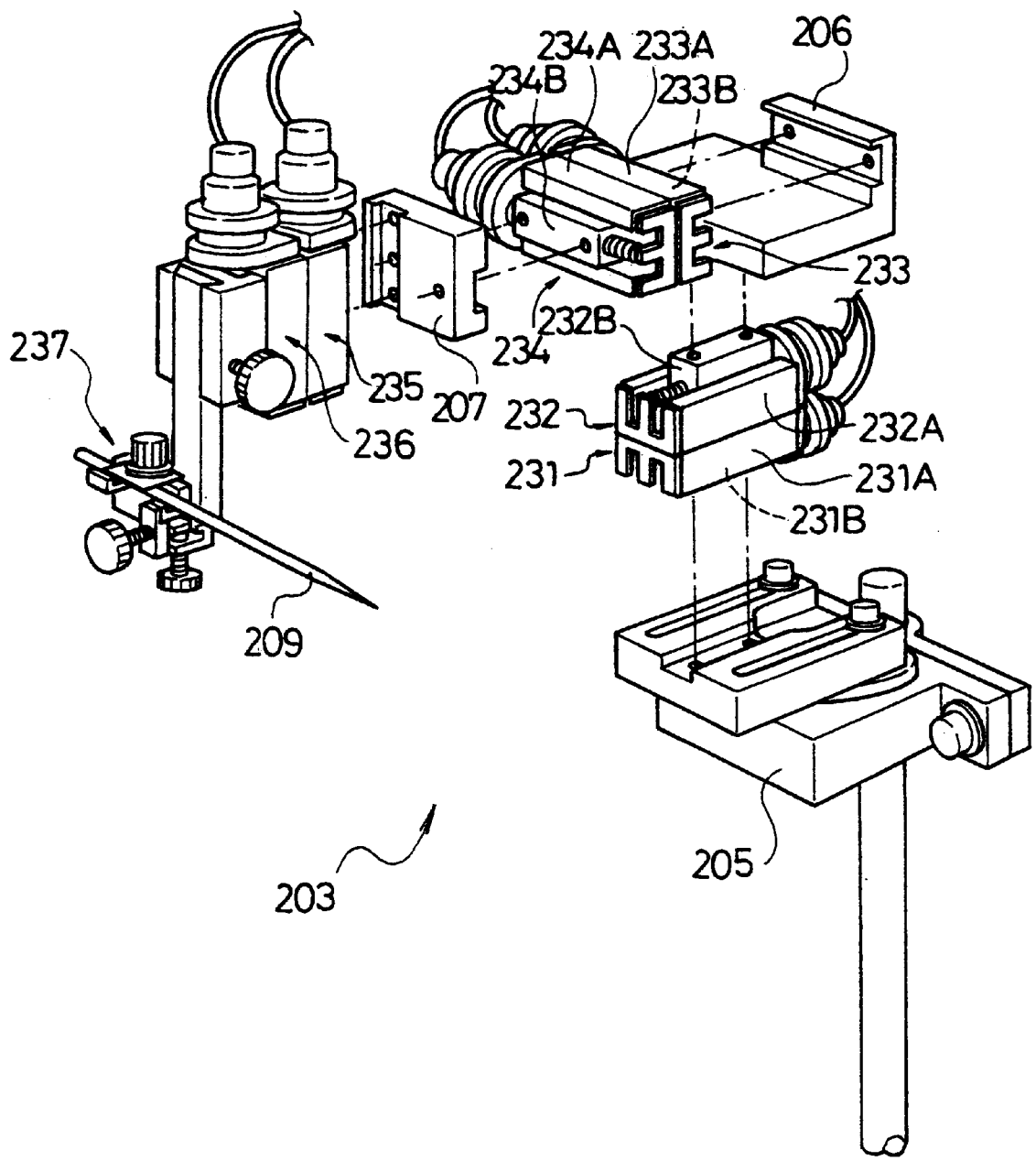
FIG. 21 is an exploded perspective view showing an actuating unit of the hydraulically-operated micromanipulator apparatus of FIG. 17.

As shown in FIG. 21, the outer slider 231A of the X-axis first slider 231 is fixed to the outer slider 232A of the X-axis second slider 232. Also, the outer slider 233A of the Y-axis first slider 233 is fixed to the outer slider 234A of the Y-axis second slider 234. The inner slider 231B of the X-axis first slider 231 is fixed to the basement 205, and the inner slider 232B of the X-axis second slider 232 is fixed to the inner slider 233B of the Y-axis first slider 233 through an angle bar 206. The inner slider 234B of the Y-axis second slider 234 is also fixed to the inner slider 235B of the Z-axis first slider 235 though a fixing element 207. By this arrangement, the microtool fixing member 237 attached to the inner slider 236B of the Z-axis second slider 236 can be movable in three dimensions, i.e. fore-and-aft, up-and-down and right-and-left directions.

Manner of operation of this hydraulically-operated micromanipulator apparatus 201 will now be described with reference to FIGS. 17 to 20.

When rotating the Z-axis coarse control dial 224 to the clockwise direction, the push portion 224E presses the sealing member 242B, thereby narrowing the second hydraulic oil chamber 242. When the volume of the second hydraulic oil chamber 242 is reduced, hydraulic fluid is flown out from the second hydraulic oil chamber 242. The hydraulic fluid from the second hydraulic oil chamber 242 is then flown through the hose 252 into the second hydraulic oil chamber 261 of the Z-axis second slider 236, thereby the inner slider 236B is displaced toward the side plate member 236H against the urging force of the spring 236I. The microtool 209 is therefore displaced toward the side plate member 236H.

When rotating the Z-axis coarse control dial 224 to the counterclockwise direction, the push portion 224E moves away from the sealing member 242B. Since the hydraulic pressure within the second hydraulic oil chamber 261 is reduced, the inner slider 236B of the Z-axis second slider 236 is moved toward the side plate member 236F by the urging force of the spring 236I. Hydraulic fluid within the second hydraulic oil chamber 261 is flown through the hose 252 into the second hydraulic oil chamber 242 of the operating unit 202. Therefore, the inner slider 236B of the Z-axis second slider 236 and the microtool 209 attached thereto are displaced toward the side plate member 236F.

Coarse control operation along the other X and Y-axes, and fine control operation along the X, Y, Z-axes are carried out by similar operations to the Z-axis coarse control operation as described above.

Figure 22:
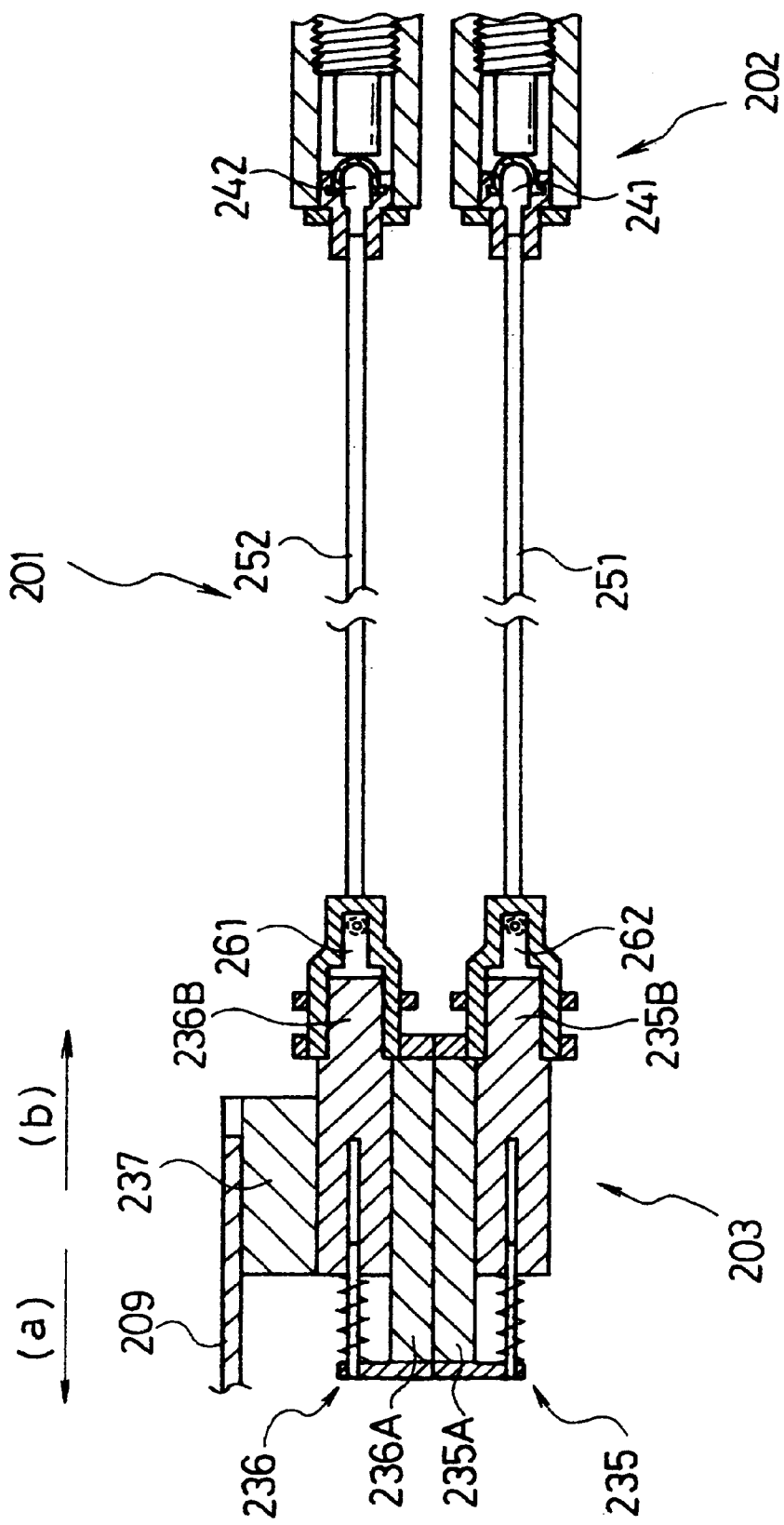
FIG. 22 is an explanatory view showing a drift-prevention mechanism of the hydraulically-operated micromanipulator apparatus of FIG. 12.

Drift-prevention mechanism will now be described with reference to FIG. 22. The volume of the first hydraulic oil chamber 241 at the operating unit 202 is the same as that of the second hydraulic oil chamber 242, while the volume of the first hydraulic oil chamber 262 at the actuating unit 203 is the same as that of the second hydraulic oil chamber 261. The amount of the hydraulic fluid within the first hydraulic oil chamber 241 of the operating unit 202 and the first hydraulic oil chamber 262 of the actuating unit 203 connected by the hose 251 (hereinafter referred to as first hydraulic fluid) is the same as that of the hydraulic fluid within the second hydraulic oil chamber 242 of the operating unit 202 and the second hydraulic oil chamber 261 of the actuating unit 203 connected by the hose 252 (hereinafter referred to as second hydraulic fluid). Here, definition of the term "same" includes minor tolerance to the extent that the relative position of the microtool 209 is substantially unchanged when the volume of hydraulic fluid is changed.

When ambient temperature changes, for example rising, both first hydraulic fluid and second hydraulic fluid within the hydraulically-operated micromanipulator apparatus 201 expand. By such expansion of the first hydraulic fluid, the volume of the first hydraulic oil chamber 262 is increased, and the outer slider 235A of the Z-axis first slider 235 is displaced to the direction shown by the arrow (b) since the inner slider 235B of the Z-axis first slider 235 is stationarily retained. Meanwhile, the volume of the second hydraulic fluid is also increased to the same amount with the first hydraulic fluid since the second hydraulic fluid is subject to such increased temperature as well. By such expansion of the second hydraulic fluid, the volume of the second hydraulic oil chamber 261 is increased, and the inner slider 236B is displaced to the direction shown by the arrow (a), opposite direction relative to the outer slider 236A.

It should be noted that the outer slider 235A of the Z-axis first slider 235 is connected to the outer slider 236A of the Z-axis second slider 236. When the outer slider 235A of the Z-axis first slider 235 is displaced to the direction shown by the arrow (b), the outer slider 236A of the Z-axis second slider 236 is also displaced together with the outer slider 235A. However, since the inner slider 236B of the Z-axis second slider 236 is displaced to the direction shown by the arrow (a), the relative position between the inner slider 236B and the inner slider 235B remains unchanged. Therefore, the microtool fixing member 237 and the microtool 209 attached thereto do not drift to the Z-axis directions when ambient temperature changes.

Contrary to the above, when ambient temperature falls, the volumes of the first hydraulic fluid and the second hydraulic fluid are both reduced. The outer slider 235A of the Z-axis first slider 235 and the outer slider 236A of the Z-axis second slider 236 are then displaced to the direction shown by the arrow (a). Meanwhile, the inner slider 236B of the Z-axis second slider 236 is displaced to the direction shown by the arrow (b), opposite direction relative to the outer slider 236A. Therefore, the relative position between the inner slider 236B and the inner slider 235B remains unchanged.

The X-axis first slider 231 and the X-axis second slider 232 are substantially the same as the Z-axis first slider 235 and the Z-axis second slider 236. Also, the Y-axis first slider 233 and the Y-axis second slider 234 are substantially the same as the Z-axis first slider 235 and the Z-axis second slider 236. Therefore, drift of the microtool 209 can be prevented for the X-axis and the Y-axis directions as well.

According to this embodiment, since the operating unit 202 is provided with two corporating hydraulic oil chambers, the amount of displacement for the microtool 209 can be doubled. Further, one hydraulic oil chamber is used for a coarse control operation to move the microtool 209 into the field of a microscope, while the other oil chamber is used for a fine control operation to finely move the microtool 209 within the field of the microscope. Therefore, not like a conventional micromanipulator apparatus, there is no need for providing a separate coarse control mechanism for the coarse control operation.

In this embodiment, the volume of the first hydraulic oil chamber 241 at the operating unit 202 is the same as that of the second hydraulic oil chamber 242, and the volume of the second hydraulic oil chamber 261 at the actuating unit 203 is the same as that of the first hydraulic oil chamber 262. However, the ratio may vary as long as the relative position between the inner slider 235B of the Z-axis first slider 235 and the inner slider 236B of the Z-axis second slider 236 is kept unchanged when ambient temperature changes. For example, the ratio of the oil chambers at the operating unit 202 to the oil chambers at the actuating unit 203 may be 1:5 for facilitating precise fine control of the microtool 209.

The hydraulically-operated micromanipulator apparatus 201 may be provided with stopper means for restricting rotation of the Z-axis coarse control dial 224 so that the amount of displacement for the inner slider 236B of the Z-axis second slider 236 can be adjustable. For example, the amount of displacement for the inner slider 236B is restricted to be in the maximum range of 1 cm. When in use, the Z-axis coarse control dial 224 is rotated to the counterclockwise direction and it is retained at the maximum rotational position. The tip end of the microtool 209 is positioned by the Z-axis fine control dial 221 in the field of the microscope. The microtool 209 is then retracted by rotating the Z-axis coarse control dial 224 to the clockwise direction until the Z-axis coarse control dial 224 abuts to the stopper means. In this position, the microtool 209 is retraced for 1 cm. After placing cells to be treated at a predetermined position, the microtool 209 is again advanced by rotating the Z-axis coarse control dial 224 to the counterclockwise direction, thereby the microtool 209 is accurately repositioned. Provision of the stopper means can eliminate a possible damage of the microtool due to contact with an obstacle upon too much displacement of the microtool. The microtool 209 is operable without electromagnetic means, which is subject to electric hindrance. Such stopper means may of course be provided with other axes.

The above hydraulically-operated micromanipulator apparatus 201 is described for three-axes movement. However, the present invention can be applied to a hydraulically-operated micromanipulator apparatus of single axis or two-axes control.

What is claimed is:

1. A hydraulically-operated micromanipulator apparatus, which comprises:
    a micromanipulator fine control unit including first and second operating-side pistons operatively related to respective first and second operating-side hydraulic cylinders and finely movable relative thereto in response to movement of a fine control device, either the operating-side pistons or the operating-side hydraulic cylinders being stationarily retained, while the non-retained operating-side pistons or cylinders are finely operable by the fine control device; and
    a hydraulically-operated micromanipulator unit including first and second actuating-side pistons operatively related to respective first and second actuating-side hydraulic cylinders and finely movable relative thereto, the actuating-side hydraulic cylinders being connected to respective operating-side hydraulic cylinders through respective hoses, either the actuating-side pistons or the actuating-side hydraulic cylinders being stationarily retained, the non-retained actuating-side pistons or cylinders being attached to a fine displacement member, whereby
    the interconnected operating-side and actuating-side cylinders compensate for pressure change of hydraulic fluid between said operating-side and actuating-side hydraulic cylinders when ambient temperature changes.

2. A hydraulically-operated micromanipulator apparatus, which comprises a micromanipulator fine control unit and a hydraulically-operated micromanipulator,
    said micromanipulator fine control unit including:
        a sliding table movable with respect to a basement;
        a first hydraulic cylinder and a second hydraulic cylinder mounted on the sliding table with openings facing outwardly along the sliding directions of the sliding table;
        a first piston and a second piston fixed to the basement and inserted within the first and the second hydraulic cylinders, respectively; and
        fine control means for finely displacing the sliding table,
    said hydraulically-operated micromanipulator including:
        an outer slider provided with guiding grooves along its sliding directions;
        an inner slider fitted within the outer slider and stationarily retained so as to ensure the sliding movement of the outer slider;
        a third hydraulic cylinder and a fourth hydraulic cylinder mounted on the outer slider with openings facing outwardly along the sliding directions of the outer slider;
        a third piston and a fourth piston fixed to the inner slider and inserted within the third and the fourth hydraulic cylinders, respectively; and
        a first hose connecting the first hydraulic cylinder and the third hydraulic cylinder, and a second hose connecting the second hydraulic cylinder and the fourth hydraulic cylinder, and
    said sliding table being finely displaced by operating the fine control means of the micromanipulator fine control unit for changing the volumes of hydraulic fluid within the first and the second hydraulic cylinders, said outer slider being finely displaced with respect to said inner slider with the volume changes of the first and the second hydraulic being transmitted through the first and the second hoses to the third and the fourth hydraulic cylinders.

3. A hydraulically-operated micromanipulator apparatus according to claim 2, wherein the volume of the hydraulic fluid within said first hydraulic cylinder is reduced when the volume of the hydraulic fluid within said second hydraulic cylinder is increased, and the volume of the hydraulic fluid within said first hydraulic cylinder is increased when the volume of the hydraulic fluid within said second hydraulic cylinder is reduced.

4. A hydraulically-operated micromanipulator apparatus according to any one of claim 2 to 3, wherein said micromanipulator fine control unit provides three-directional fine displacement of the hydraulically-operated micromanipulator.

5. A hydraulically-operated micromanipulator apparatus, which comprises a micromanipulator fine control unit and a hydraulically-operated micromanipulator,
    said micromanipulator fine control unit including:
        first and second hydraulic cylinders; first and second pistons inserted within the corresponding first and second hydraulic cylinders; an operating-side slider comprising a movable member and a stationary member; and a fine control means for finely controlling the operating-side slider;
        either said first piston or said first hydraulic cylinder being stationary held, while the other is mounted on the movable member of said operating-side slider, and
    said hydraulically-operated micromanipulator including:
        a third hydraulic cylinder connected to said first hydraulic cylinder through a first hose; a fourth hydraulic cylinder connected to said second hydraulic cylinder through a second hose; third and fourth pistons inserted within the corresponding third and fourth hydraulic cylinders; and an actuating-side slider comprising a movable member and a stationary member;

either said third piston or said third hydraulic cylinder being stationarily held, while the other is mounted on the movable member of said actuating-side slider, and either said fourth piston or said fourth hydraulic cylinder being stationarily held, while the other is mounted on the movable member of said operating-side slider, the movable member of said operating-side slider being displaced by operating the fine control means of the micromanipulator fine control unit for changing the volumes of hydraulic fluid within the first and the second hydraulic cylinders, while said movable member of said actuating-side slider is finely displaced with respect to the stationary member of said actuating-side slider with the volume change of the first and the second hydraulic cylinders being transmitted through the first and the second hoses to the third and fourth hydraulic cylinders, and a volume change of hydraulic fluid resulting from ambient temperature changes between the micromanipulator fine control unit and the hydraulically-operated micromanipulator being prevented by the first and the second hydraulic cylinders and the third and the fourth hydraulic cylinders being connected through the first and the second hoses.

6. A hydraulically-operated micromanipulator apparatus according to claim 5, wherein the volume of the hydraulic fluid within said first hydraulic cylinder is reduced when the volume of the hydraulic fluid within said second hydraulic cylinder is increased, and the volume of the hydraulic fluid within said first hydraulic cylinder is increased when the volume of the hydraulic fluid within said second hydraulic fluid is reduced.

7. A hydraulically-operated micromanipulator apparatus according to claim 6, wherein said micromanipulator fine control unit provides three-directional fine displacement of the hydraulically-operated micromanipulator.

* * * * *